US009433695B2

(12) United States Patent
Aamodt et al.

(10) Patent No.: US 9,433,695 B2
(45) Date of Patent: Sep. 6, 2016

(54) SYSTEMS, APPARATUS, METHODS AND ARTICLES FOR USE IN SANITIZATION OR DISINFECTION

(71) Applicant: Diligence Corp., Vancouver, WA (US)

(72) Inventors: James Alan Aamodt, Hood River, OR (US); John William Mayer, Vancouver, WA (US); Christopher Adam Thompson, Hood River, OR (US); James Van't Slot, Seattle, WA (US)

(73) Assignee: DILIGENCE CORPORATION, Vancouver, WA (US)

( * ) Notice: Subject to any disclaimer, the term of this patent is extended or adjusted under 35 U.S.C. 154(b) by 421 days.

(21) Appl. No.: 13/789,466

(22) Filed: Mar. 7, 2013

(65) Prior Publication Data
US 2013/0183749 A1  Jul. 18, 2013

Related U.S. Application Data

(63) Continuation of application No. PCT/US2011/050715, filed on Sep. 7, 2011.

(60) Provisional application No. 61/433,774, filed on Jan. 18, 2011.

(51) Int. Cl.
*G01N 1/00* (2006.01)
*A61L 9/14* (2006.01)
*A61L 2/22* (2006.01)

(52) U.S. Cl.
CPC .. *A61L 9/14* (2013.01); *A61L 2/22* (2013.01); *A61L 2202/122* (2013.01); *A61L 2202/14* (2013.01)

(58) Field of Classification Search
CPC ........ A61L 2/22; A61L 9/14; A61L 2202/14

USPC ...................................... 422/3, 119
See application file for complete search history.

(56) References Cited

U.S. PATENT DOCUMENTS 6,537,491 B1 *  3/2003  Wang et al. ....................... 422/3
8,889,081 B2 * 11/2014  Schwartz et al. ............. 422/292

(Continued)

FOREIGN PATENT DOCUMENTS

GB     1014820     12/1965
GB     1115339      5/1968

(Continued)

OTHER PUBLICATIONS

International Search Report, mailed Apr. 30, 2012, for International Application No. PCT/US2011/050715, 4 pages.
Written Opinion, mailed Apr. 30, 2012, for International Application No. PCT/US2011/050715, 3 pages.

*Primary Examiner* — Kevin Joyner
(74) *Attorney, Agent, or Firm* — Seed IP Law Group PLLC

(57) ABSTRACT

Various devices allow for sanitization or disinfection by exhausting a dry fog biocide agent into an ambient environment. A nebulizer, for instance a vibrator that oscillates or vibrates at ultrasonic frequencies, nebulizes a biocide agent, for instance chlorine dioxide, peracetic acid, hydrogen peroxide, to create the dry fog. Such devices may withdraw the dry fog or biocide agent from the ambient environment after some period of time. Operational parameters of the devices may be tracked or monitored. Each device may implement tracking or monitoring. Additionally or alternatively, a separate tracking or monitoring system may track or monitor the operational parameters of one or more devices. Tracking or monitoring may include exception reporting, as well as other reporting.

15 Claims, 12 Drawing Sheets

(56) References Cited

U.S. PATENT DOCUMENTS

| | | |
|---|---|---|
| 2003/0170901 A1 | 9/2003 | Kippenhan et al. |
| 2008/0038166 A1* | 2/2008 | Hill ................... A61L 2/208 422/292 |
| 2009/0313071 A1 | 12/2009 | Hehenberger et al. |
| 2010/0095983 A1 | 4/2010 | Barnhill et al. |

FOREIGN PATENT DOCUMENTS

| | | |
|---|---|---|
| WO | 2005/048041 A2 | 5/2005 |
| WO | 2012/032338 A1 | 3/2012 |

* cited by examiner

```
                      ┌─────────────────────────┐ ┌─502
                      │  Start disinfection cycle│
                      └─────────────────────────┘
                                   │
                                   ▼
                      ┌─────────────────────────┐ ┌─504
                      │  Nebulize biocide agent(s)│
                      └─────────────────────────┘
                                   │
                                   ▼
         ┌──────────────────────────────────────────────┐ ┌─506
         │  Distribute biocide agent(s) as dry fog from │
         │  disinfection system into ambient environment│
         └──────────────────────────────────────────────┘
                                   │
                                   ▼
              ┌──────────────────────────────────┐ ┌─508
              │  Extract dry fog from ambient    │
              │  environment into disinfection system│
              └──────────────────────────────────┘
                                   │
                                   ▼
                      ┌─────────────────────────┐ ┌─510
                      │  End disinfection cycle │
                      └─────────────────────────┘
```

*FIG.5*

```
                    ┌──────────────────────────────┐
                    │ Vibrate at ultrasonic frequency │─ 602
                    └──────────────┬───────────────┘
                                   ▼
                    ┌──────────────────────────────┐
                    │ Impart vibration to biocide agent(s) │─ 604
                    └──────────────┬───────────────┘
                                   ▼
                 ┌────────────────────────────────────┐
                 │ Operate fan(s) to blow nebulized biocide │─ 606
                 │   agent from disinfection system   │
                 └────────────────┬───────────────────┘
                                  ▼
              ┌────────────────────────────────────────┐
              │ Operate fan(s) to draw dry fog containing │─ 608
              │ nebulized biocide agent(s) into disinfection │
              │      system from ambient environment      │
              └────────────────┬───────────────────────┘
                               ▼
             ┌──────────────────────────────────────────┐
             │ Condense at least some water vapor from dry │─ 610
             │   fog extracted from ambient environment   │
             └────────────────┬─────────────────────────┘
                              ▼
                   ┌──────────────────────────┐
                   │ Recycling water condensed │─ 612
                   │    from the water vapor   │
                   └─────────────┬────────────┘
                                 ▼
                   ┌──────────────────────────┐
                   │   Treat extraction stream │─ 614
                   │  from ambient environment │
                   └─────────────┬────────────┘
                                 ▼
           ┌────────────────────────────────────────────┐
           │ Automatically control operation of component(s) │─ 616
           │     in response to sensed characteristic      │
           └────────────────────────────────────────────┘
```

*FIG. 6*

```
                 ┌─────────────────────────────┐
                 │ Filter biocide agent(s)     │─ 702
                 │ extracted from ambient      │
                 │ environment                 │
                 └─────────────┬───────────────┘
                               ▼
                 ┌─────────────────────────────┐
                 │ Catalyze biocide agent(s)   │─ 704
                 │ extracted from ambient      │
                 │ environment                 │
                 └─────────────┬───────────────┘
                               ▼
                 ┌─────────────────────────────┐
                 │ Electro-statically charge   │─ 706
                 │ biocide agent(s) extracted  │
                 │ from ambient environment    │
                 └─────────────┬───────────────┘
                               ▼
                 ┌─────────────────────────────┐
                 │ Expose biocide agent(s)     │─ 708
                 │ extracted from ambient      │
                 │ environment to ultraviolet  │
                 │ light                       │
                 └─────────────────────────────┘
```

801 Initiation / Handshaking

802 Receive signals at recording module from sensor(s) indicative of dry fogging biocide disinfection operating parameters 804 Produce compliance report(s) by a reporting module based at least in part on the dry fogging biocide disinfection operating parameters 806 Identify by exception reporting module exceptions between dry fogging biocide disinfection operating parameter(s) and nominal dry fogging biocide disinfection operating parameter(s)

808 Automatically provide notification occurrence of exception by exception reporting module 810 Archive copy of compliance report in date and time stamped tamper indicative form 812 Provide copy of compliance report to corporate management system 814 Provide copy of compliance report to insurer or compliance verification organization system

FIG. 8

SYSTEMS, APPARATUS, METHODS AND ARTICLES FOR USE IN SANITIZATION OR DISINFECTION

BACKGROUND

1. Technical Field

The present disclosure generally relates to the field of sanitization or disinfection, for example sanitizing or disinfecting environments, rooms, areas, surfaces or objects, for instance for use in medical facilities such as hospitals or clinics in which medical procedures may be performed.

2. Description of the Related Art

In many instances it is useful to disinfect, sterilize or otherwise sanitize environments, rooms, areas, surfaces or objects, and in some situations such may even be vitally important.

For example, it is typically important to sterilize, disinfect or otherwise sanitize environments and objects associated with a medical treatment and diagnostic procedures, for instance medical procedures such as a surgery, child birth delivery, and physical examinations, or even diagnostic procedures such as medical imaging procedures.

Conventional techniques for sterilizing, disinfecting or otherwise sanitizing reusable instruments or implements (e.g., scalpels, scissors, forceps, hemostats, and/or clamps) typically include exposing the instruments or implements to high temperatures and pressures (e.g., autoclaving), chemically treating the instruments or implements (e.g., bleaching), and/or exposing the instruments or implements to ultraviolet light. Conventional techniques for sterilizing, disinfecting or otherwise sanitizing other non-disposable objects (e.g., linens, sheets, towels) may include laundering using water at suitably hot temperatures and/or a sanitizing agent (e.g., bleach). Also for example, disposable objects (e.g., surgical sponges, gauzes, absorbent pads) may be supplied from the manufacturer in sterile form in suitable packaging. Conventional techniques for sterilizing, disinfecting or otherwise sanitizing surfaces in rooms (e.g., floors, walls, counters, table tops) in which medical procedures are performed typically include wiping or mopping the surfaces with a disinfectant solution.

These sanitizing or disinfecting procedures are typically performed by low wage workers, who may not have the training or motivation to do a thorough job. Even if properly trained and motivated, there may not be adequate time or staff provided to thoroughly prepare an environment. In many instances, there is little oversight over such procedures.

Tracking sterilization, disinfection or sanitization may also be useful. Such may be useful in ensuring that adequate precautions are being taken. Conventional techniques for tracking such typically include filling out or completing a paper form by an individual who performs the sterilization, disinfection or sanitation procedures. Again, these procedures are typically performed by low wage workers, who may not have the training or motivation to do a thorough job, or who may be overworked. In many instances, forms are not filled out concurrently with the procedures, but may completed at the end of a work shift or even work week, increasing the probability of the recorded information being inaccurate. Again, there may be little or no oversight in how and when such forms are completed.

Sterilization, disinfection or sanitizing is becoming increasingly important as bacteria, viruses and/or fungi mutate and particularly as antibiotic or drug resistant strains of infectious organisms (e.g., Methicillin-Resistant *Staphylococcus Aureus*, commonly denominated as MRSA) become ever more prevalent. Many such antibiotic or drug resistant infections are acquired in medical facilities, such as hospitals. Thus, new approaches to sanitizing and disinfecting, including new approaches to tracking such procedures are desirable.

BRIEF SUMMARY

As an overview, various devices allow for sanitization or disinfection by exhausting a dry fog biocide agent or decontaminant into an ambient environment. Such devices may include a nebulizer, for instance, an vibrator that oscillates or vibrates at ultrasonic frequencies to nebulizer a biocide agent, for instance chlorine dioxide or peracetic acid, to create the dry fog. Such devices may withdraw the dry fog or biocide agent from the ambient environment after some period of time. Operational parameters of the devices may be tracked or monitored. Each device may implement tracking or monitoring. Additionally or alternatively, a separate tracking or monitoring system may track or monitor the operational parameters of one or more devices. Tracking or monitoring may include exception reporting, as well as other reporting.

Sanitization or disinfection may be useful in medical care environments, for instance hospitals, clinics, physician offices, urgent care facilities, imaging or radiological facilities. Sanitization or disinfection may also be useful in other environments, such as public or private facilities in which people gather, reside or are confined or in which consumable products such as food or beverages are prepared, processed, or packaged. Such environments may, for example include sports arenas or stadiums, theaters, amusement parks, museums, exhibition halls, or convention centers. Such environments may, for example, include conveyances such as trains, ships, airplanes, buses, trucks, and associated facilities such as terminals, stations, waiting areas or rooms, loading docks, or warehouses. Such environments may, for example include apartment houses or blocks, public housing, hotels, motels, barracks, or camp bunkhouses. Such environments may, for example include jails, prisons or other detention facilities. Such environments may include kitchens, factories, and various food processing or packaging facilities. Such environments may also include areas or facilities in which foods and/or beverages are prepared, processed and/or distributed such as fields, harvest collection points, kitchens, processing lines, warehouses, and/or grocery or produce markets.

Such an approach may conveniently, thoroughly sterilize, disinfect or otherwise sanitize an entire environment, including all surfaces and objects in the environment, as well as ambient air in the environment. Surfaces may, for example, include floors, walls, counters, tables, and operating tables. Surfaces may also include surfaces that may not typically be sanitized on a regular basis such as drapes, blinds, furnishings, fixtures, beds, mattresses. Surfaces may also include surfaces that are difficult to sanitize such as ceilings, undersides of counters, tables, furnishings, fixtures, beds, mattresses, and various other areas that are difficult to reach or access. Sanitizing objects may be in addition to conventional sterilizing procedures such as autoclaving.

As noted above, tracking sterilization, disinfection or other sanitation procedures may also be useful. Such may not only be useful in ensuring that adequate precautions are being taken, but may also be useful in defending against liability claims, as well as meeting requirements imposed by insurers and/or governmental mandates.

A disinfection system useful in disinfection or sterilization may be summarized as including at least one reservoir to hold at least one biocide agent; means for distributing the at least one biocide agent from the at least one reservoir into an ambient environment as a dry fog; and means for extracting at least some of the dry fog from the ambient environment.

The means for distributing the at least one biocide agent may include at least one nebulizer. The at least one nebulizer may include a transducer selectively operable to vibrate at one or more ultrasonic frequencies. The means for distributing the at least one biocide agent may include at least one fan selectively operable to exhaust at least some of the biocide agent in a nebulized form into the ambient environment from the disinfection system. The means for extracting at least some of the at least one biocide agent may include at least one fan selectively operable to extract at least some of the biocide agent from the ambient environment into the disinfection system. The means for extracting at least some of the at least one biocide agent may include at least one condensation subsystem selectively operable to condense at least some vapor from the dry fog extracted from the ambient environment.

The disinfection system may further include means for treating at least some of the biocide agent extracted from the ambient environment. The means for treating at least some of the biocide agent extracted from the ambient environment may include at least one of an activated carbon filter, high efficiency particulate (HEPA) filter, a quantity of Zeolite, a porous material impregnated with a reducing agent, an electrostatic element or a source of ultraviolet light.

Means for extracting may be fluidly coupled to recycle at least some biocide agent extracted from the ambient environment to the at least one reservoir.

The disinfection system may further include a quantity of chlorine dioxide received in the at least one reservoir as at least one biocide agent.

A disinfection system useful in sterilization of an environment, may be summarized as including at least one reservoir to hold at least one biocide agent; at least one nebulizer coupled to receive the at least one biocide agent from the at least one reservoir and selectively operable to nebulize the received one biocide agent; one or more fans, at least one of the one or more fans selectively operable to exhaust at least some of the nebulized biocide agent from the disinfection system into an ambient environment as a dry fog during a first portion of a disinfection cycle, at least one of the one or more fans selectively operable to extract at least some of the biocide agent in the form of the dry fog from the ambient environment into the disinfection system during a second portion of the disinfection cycle.

The at least one nebulizer may include a transducer operable to vibrate at one or more ultrasonic frequencies. At least a first one of the one or more fans may be selectively operable to exhaust at least some of the nebulized biocide agent into the ambient environment during the first portion of the disinfection cycle and to extract at least some of the nebulized biocide agent in the form of the dry fog from the ambient environment during the second portion of the disinfection cycle.

The disinfection system may further include a condensation subsystem selectively operable to condense at least some vapor from the dry fog extracted from the ambient environment.

The condensation subsystem may include at least one condensation element having at least one channel, a heat transfer medium that cycles through the passage of the at least one condensation element, and at least one compressor coupled to compress the heat transfer medium, the at least one condensation element positioned such that at least some of the biocide agent in the form of the dry fog extracted from the ambient environment contacts the at least one condensation element.

The disinfection system may further include at least one conduit fluidly coupled to recycle at least some of the vapor condensed from the dry fog extracted from the ambient.

The disinfection system may further include at least one of an activated carbon filter, a quantity of Zeolite, or a porous material impregnated with a reducing agent, positioned to physically contact at least some of the biocide agent extracted from the ambient environment.

The disinfection system may further include at least one of an electrostatic element or a source of ultraviolet light positioned to expose at least some of the biocide agent extracted from the ambient environment.

The disinfection system may further include a quantity of a first biocide agent and at least a second biocide agent received in the at least one reservoir as at least one biocide, the first and the second biocide agents selected from chlorine dioxide, peracetic acid, hydrogen peroxide and electrochemically activated solutions (e.g., electrolyzed water).

At least one component of the disinfection system may be configured to exhaust at least the first and the second biocide agents into the ambient environment in a defined order.

The disinfection system may further include a conditioning subsystem selectively operable to adjust at least one of a temperature, a humidity, or an amount of ozone at least one of immediately before, during or immediately following a least one of exhaustion of at least some of the nebulized biocide agent from the disinfection system into an ambient environment or extraction of at least some of the biocide agent from the ambient environment.

The condition system may be configured to vary a humidity of the ambient environment to a defined relative humidity. At least one component of the disinfection system may be automatically responsive to at least one sensed characteristic in the ambient environment, the at least one sensed characteristic selected from the group consisting of: a concentration of a biocide agent being exhausted, a concentration of biocide agent in the ambient environment, a pathogen test result or an organic matter test result, a presence of a biocide agent on at least one surface in the ambient environment, a time of exposure, and a surface wetness.

A method of operating a disinfection system may be summarized as including, during a first portion of a disinfection cycle, distributing the at least one biocide agent from the disinfection system into an ambient environment as a dry fog; and during a second portion of the disinfection cycle, extracting at least some of the dry fog from the ambient environment into the disinfection system.

Distributing the at least one biocide agent from the disinfection system into an ambient environment as a dry fog may include nebulizing the biocide agent. Nebulizing the biocide agent may include vibrating a transducer at an ultrasonic frequency and imparting the vibration to at least some of the biocide agent to produce nebulized biocide agent. Distributing the at least one biocide agent into the ambient environment may include operating at least one fan to blow the nebulized biocide agent from disinfection system into the ambient environment. Extracting the at least one biocide agent from the ambient environment may include operating at least one fan to draw at least some of the nebulized biocide agent into the disinfection system from the ambient environment.

The method of operating a disinfection system may further include condensing at least some water vapor from the dry fog extracted the ambient environment. The method of operating a disinfection system may further include recycling water condensed from the water vapor.

The method of method of operating a disinfection system may further include treating at least some of the at least one biocide agent extracted from the ambient environment.

Treating at least some of the at least one biocide agent extracted from the ambient environment may include filtering at least some of the at least one biocide agent extracted from the ambient environment. Treating at least some of the at least one biocide agent extracted from the ambient environment may include catalyzing at least some of the at least one biocide agent extracted from the ambient environment. Treating at least some of the at least one biocide agent extracted from the ambient environment may include electro-statically charging at least some of the at least one biocide agent extracted from the ambient environment. Treating at least some of the at least one biocide agent extracted from the ambient environment may include exposing at least some of the at least one biocide agent extracted from the ambient environment to ultraviolet light. Distributing the at least one biocide agent from the disinfection system into an ambient environment as a dry fog during the first portion of the disinfection cycle may include distributing a first and at least a second biocide agent into the ambient environment in a defined order.

The method of operating a disinfection system may further include adjusting a temperature or a humidity of air at least one of immediately before, during or immediately following the disinfection cycle.

Adjusting a temperature or a humidity of air at least one of immediately before, during or immediately following the disinfection cycle may include varying a humidity of the ambient environment to a defined relative humidity.

The method of method of operating a disinfection system may further include automatically controlling at least one operation of the disinfection system in response to at least one sensed characteristic in the ambient environment, the at least one sensed characteristic selected from the group consisting of: a concentration of a biocide agent being exhausted, a concentration of biocide agent in the ambient environment, a pathogen test result or an organic matter test result, a presence of a biocide agent on at least one surface in the ambient environment, a time of exposure, and a surface wetness.

A system for use in sterilization may be summarized as including a recording module communicatively coupled to receive signals from at least one sensor indicative of dry fogging biocide disinfection operating parameters, including an indication of when a disinfection cycle starts and an indication of when the disinfection cycle ends; and a reporting module configured to produce compliance reports based at least in part on the dry fogging biocide disinfection operating parameters indicated by the received signals.

The signals from the at least one sensor indicative of dry fogging biocide disinfection operating parameters may further include an indication of an identity of an end user operator who operates a dry fogging biocide disinfection apparatus. The signals from the at least one sensor indicative of dry fogging biocide disinfection operating parameters may further include an indication of a volume of a biocide agent contained in a reservoir of a dry fogging biocide disinfection apparatus used at least one of immediately before, during or immediately following the disinfection cycle. The signals from the at least one sensor indicative of dry fogging biocide decontamination operating parameters may further include an indication of an equipment identifier that uniquely identifies a dry fogging biocide decontamination apparatus operated during the decontamination cycle. The signals from the at least one sensor may be indicative of a concentration of a biocide agent being exhausted from a dry fogging biocide decontamination apparatus during at least some portion of the decontamination cycle.

The recording module may be further communicatively coupled to receive signals indicative of a concentration of biocide agent in the ambient environment at least one of immediately before, during or immediately following the decontamination cycle, and the reporting module may be further configured to produce the compliance reports based at least in part on the concentration of biocide agent in the ambient environment. The recording module may be further communicatively coupled to receive signals indicative of at least one of a pathogen test result or an organic matter test result of at least one surface in the ambient environment sampled at least one of immediately before, during or immediately following the decontamination cycle, and the reporting module may be further configured to produce the compliance reports based at least in part on the pathogen or the organic matter test results. The recording module may be further communicatively coupled to receive signals indicative of a result of at least one test of a presence of a biocide agent on at least one surface in the ambient environment sampled at least one of immediately before, during or immediately following the decontamination cycle, and the reporting module may be further configured to produce the compliance reports based at least in part on the result of the at least one test of the presence of the biocide agent on the at least one surface.

The system for use in sterilization may further include an exception reporting module configured to identify exceptions between at least one of the dry fogging biocide decontamination operating parameters and at least one nominal dry fogging biocide decontamination operating parameter; and provide a notification of the occurrence of an exception.

The exception reporting module may provide the notification of the occurrence of an exception in real-time. The exception reporting module may provide the notification of the occurrence of an exception in a periodic compliance report.

The system for use in sterilization may further include at least one at least one processor; and at least one non-transitory processor-readable storage medium communicatively coupled to the at least one processor and which stores at least one of processor executable instructions or data.

The recording module may be implemented by the at least one processor executing a first number of instructions stored in the at least one non-transitory processor-readable storage medium and the reporting module may be implemented by the at least one processor executing a second number of instructions stored in the at least one non-transitory processor-readable storage medium. The system may be a backend system and may further include a communications interface communicatively coupled to receive information from a plurality of dry fogging biocide decontamination apparatus.

The reporting module may be further configured to archive a copy of a compliance report in a date and time stamped tamper indicative form. The reporting module may be further configured to provide a copy of a compliance report to an insurer or compliance verification organization. The reporting module may provide a compliance report in at least two colors, the colors indicative of respective ones of at least two different levels of compliance. The reporting module may receive information from a scheduling module indicative of scheduling of a set of medical procedures for each of a plurality of rooms in a facility and the reporting module provides a compliance report that represents for each respective room of the facility each of a number of decontamination cycles relative to the medical procedures scheduled the respective room. The reporting module may provide the compliance report in the form of at least one timeline, with a set of graphical indications presented along the timeline representing the decontamination cycles performed and the procedures scheduled for each of the rooms of the facility. The reporting module may provide a compliance report in the form of graphical representation of the facility with a set of graphical indications presented associated with respective ones of the rooms representing the decontamination cycles performed and the procedures scheduled for each of the rooms of the facility. The reporting module may provide a compliance report in the form of graphical representation of a facility with at least two rooms, with a set of graphical indications presented associated with respective ones of the rooms representing the decontamination cycles performed for the room.

The system for use in sterilization may be part of a dry fogging biocide decontamination apparatus, and may further include a reservoir to hold a biocide; at least one nebulizer coupled to receive the at least one biocide agent from the at least one reservoir and selectively operable to nebulize the received one biocide agent; one or more fans, at least one of the one or more fans selectively operable to exhaust at least some of the nebulized biocide agent from the decontamination system into an ambient environment as a dry fog during a first portion of a decontamination cycle, at least one of the one or more fans selectively operable to extract at least some of the biocide agent in the form of the dry fog from the ambient environment into the decontamination system during a second portion of the decontamination cycle.

The at least one sensor may include at least one detector positioned to detect an amount of biocide agent in the reservoir. The at least one sensor may include at least one sensor operable to detect a concentration of a biocide in the dry fog exhausted from a dry fogging biocide decontamination system. The at least one sensor may include at least one machine-readable data carrier reader. The at least one machine-readable data carrier reader may include at least one of a machine-readable symbol reader operable to optically read information encoded in machine-readable symbols or a radio frequency identification (RFID) operable to read information encoded in RFID transponders. The at least one sensor may include at least sensor operable to detect a concentration of a biocide in the dry fog in the ambient environment at least one of immediately before, during or immediately following the decontamination cycle.

A method for use in sterilization may be summarized as including receiving signals at a recording module from at least one sensor, the signals indicative of dry fogging biocide decontamination operating parameters, including an indication of when a decontamination cycle starts and an indication of when the decontamination cycle ends; and producing compliance reports by a reporting module based at least in part on the dry fogging biocide decontamination operating parameters indicated by the received signals.

Receiving signals at a recording module may include receiving an indication of an identity of an end user operator who operates a dry fogging biocide decontamination apparatus. Receiving signals at a recording module may include an indication of a volume of a biocide agent contained in a reservoir of a dry fogging biocide decontamination apparatus used at least one of immediately before, during or immediately following the decontamination cycle. Receiving signals at a recording module may include an indication of an equipment identifier that uniquely identifies a dry fogging biocide decontamination apparatus operated during the decontamination cycle. Receiving signals at a recording module may include receiving an indication of a concentration of a biocide agent being exhausted from a dry fogging biocide decontamination apparatus during at least some portion of the decontamination cycle. Receiving signals at a recording module may include receiving signals indicative of a concentration of biocide agent in the dry fog in the ambient environment at least one of immediately before, during or immediately following the decontamination cycle, and producing the compliance reports by the reporting module may include producing the compliance reports based at least in part on the concentration of biocide agent in the dry fog in the ambient environment.

Receiving signals at a recording module may include receiving signals indicative of at least one of a pathogen test or an organic material test result of at least one surface in the ambient environment sampled at least one of immediately before, during or immediately following the decontamination cycle, and producing the compliance reports by the reporting module may include producing the compliance reports based at least in part on the pathogen or the organic material test results. Receiving signals at a recording module may include receiving signals indicative of a result of at least one test of a presences of a biocide agent on at least one surface in the ambient environment sampled at least one of immediately before, during or immediately following the decontamination cycle, and producing the compliance reports by the reporting module may include producing the compliance reports based at least in part on the result of the at least one test of the presence of the biocide agent on the at least one surface.

The method for use in sterilization may further include identifying by an exception reporting module exceptions between at least one of the dry fogging biocide decontamination operating parameters and at least one nominal dry fogging biocide decontamination operating parameter; and automatically providing a notification of the occurrence of an exception by the exception reporting module.

The providing a notification of the occurrence of an exception may include providing the notification in real-time. Providing the notification of the occurrence of an exception may include providing the notification in a periodic compliance report. Receiving signals at a recording module from at least one sensor may include receiving signals from a plurality of dry fogging biocide decontamination apparatus.

The method for use in sterilization may further include archiving by the reporting module a copy of a compliance report in a date and time stamped tamper indicative form.

The method for use in sterilization may further include providing by the reporting module a copy of a compliance report to an insurer system or compliance verification organization system.

Providing a compliance report may include providing the compliance report in at least two colors, the colors indicative of respective ones of at least two different levels of compliance.

The method for use in sterilization may further include receiving information from a scheduling module by the reporting module, the information indicative of scheduling of a set of medical procedures for each of a plurality of rooms in a facility and wherein providing compliance reports by the reporting module includes providing a compliance report that represents for each respective room of the facility each of a number of decontamination cycles relative to the medical procedures scheduled the respective room.

Providing a compliance report may include providing the compliance report in the form of at least one timeline, with a set of graphical indications presented along the timeline representing the decontamination cycles performed and the procedures scheduled for each of the rooms of the facility. Providing compliance reports by the reporting module may include providing a compliance report in the form of graphical representation of the facility with a set of graphical indications presented associated with respective ones of the rooms representing the decontamination cycles performed and the procedures scheduled for each of the rooms of the facility. Providing compliance reports by the reporting module may include providing a compliance report in the form of graphical representation of a facility with at least two rooms, with a set of graphical indications presented associated with respective ones of the rooms representing the decontamination cycles performed for the room.

Receiving signals at a recording module may include receiving an indication of an identity of a room in which a dry fogging biocide decontamination apparatus is located.

The method for use in sterilization may further include establishing a logical association by at least one processor between a room in which a dry fogging biocide decontamination apparatus is located and a particular use assigned to the room.

The method for use in sterilization may further include establishing a logical association by at least one processor between a room in which a dry fogging biocide decontamination apparatus is located and a set of standard sanitation operating protocols for a use assigned to the room.

The method for use in sterilization may further include establishing a logical association by at least one processor between a set of sensors including at least one sensor and a set of standard sanitation operating protocols for a use assigned to the room.

The method for use in sterilization may further include identifying by an exception reporting module any exceptions between at least one sensed characteristic sensed by the at least one sensor and at least one nominal characteristic as specified by the set of standard sanitation operating protocols; and automatically providing a notification of the occurrence of an exception by the exception reporting module.

The method for use in sterilization may further include identifying by an exception reporting module any exceptions between at least one sensed characteristic sensed by the at least one sensor and at least one nominal characteristic as specified by the set of standard sanitation operating protocols; and automatically identifying by at least one processor a set of corrective actions including at least one corrective action that addresses at least one identified exception; and providing an end user with the set of corrective actions.

The method for use in sterilization may further include recording by the recording module which corrective actions were taken along with an identifier indicating an identity of any end user that took any of the corrective actions.

The method for use in sterilization may further include, for each procedure of a number of procedures specified by the standard sanitation operating protocol, recording by the recording module an indication of whether the procedure has been performed.

The method for use in sterilization may further include electronically transferring by the reporting module data collected via the at least one sensor to a computing system of at least one of a department management, hospital management, corporate management, or insurer in an enterprise format.

The method for use in sterilization may further include electronically transferring by the reporting module at least one of an exception report or a trends analysis to a number of computing systems associated with various hierarchical levels in corporate enterprise system.

The method for use in sterilization may further include electronically transferring by the reporting module at least one of a pass/fail indication and a user selectable indicia selection of which provides a drill down to report sensor data associated with the respective pass/fail indication as collected by the recording module.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 5 is a flow diagram of a high level method of operating an interrogation and detection system to exhaust and then extract a dry fog or biocide agent(s) into an ambient environment, according to one illustrated embodiment.

FIG. 6 us a flow diagram of a low level method of operating a disinfection system to exhaust a dry fog or biocide agent(s) into an ambient environment, according to one illustrated embodiment.

FIG. 7 is a flow diagram of a low level method of operating a disinfection system to extract a dry fog or biocide from an ambient environment, according to one illustrated embodiment.

FIG. 8 is a flow diagram of a high level method of operating a system to track operation of one or more disinfection systems, according to one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, transceivers, networks, servers, and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless the context makes clear otherwise, the terms sterilization, disinfection and sanitation, and variations thereof (e.g., sterilizing, disinfecting, sanitizing) are used interchangeably herein and in the claims. Unless the context makes clear otherwise, the terms biocide agent refers to a decontaminant or biocide whether dry, in solution, or in gaseous form. Thus, nebulizing or nebulization of biocide agent may, for example include nebulizing or nebulization of a dry form of the biocide agent to produce fine particles thereof, or may include nebulizing or nebulization of a fluid form of a biocide agent, for example a biocide agent solution in which a quantity of a biocide agent is mixed in a quantity of fluid (e.g., water).

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
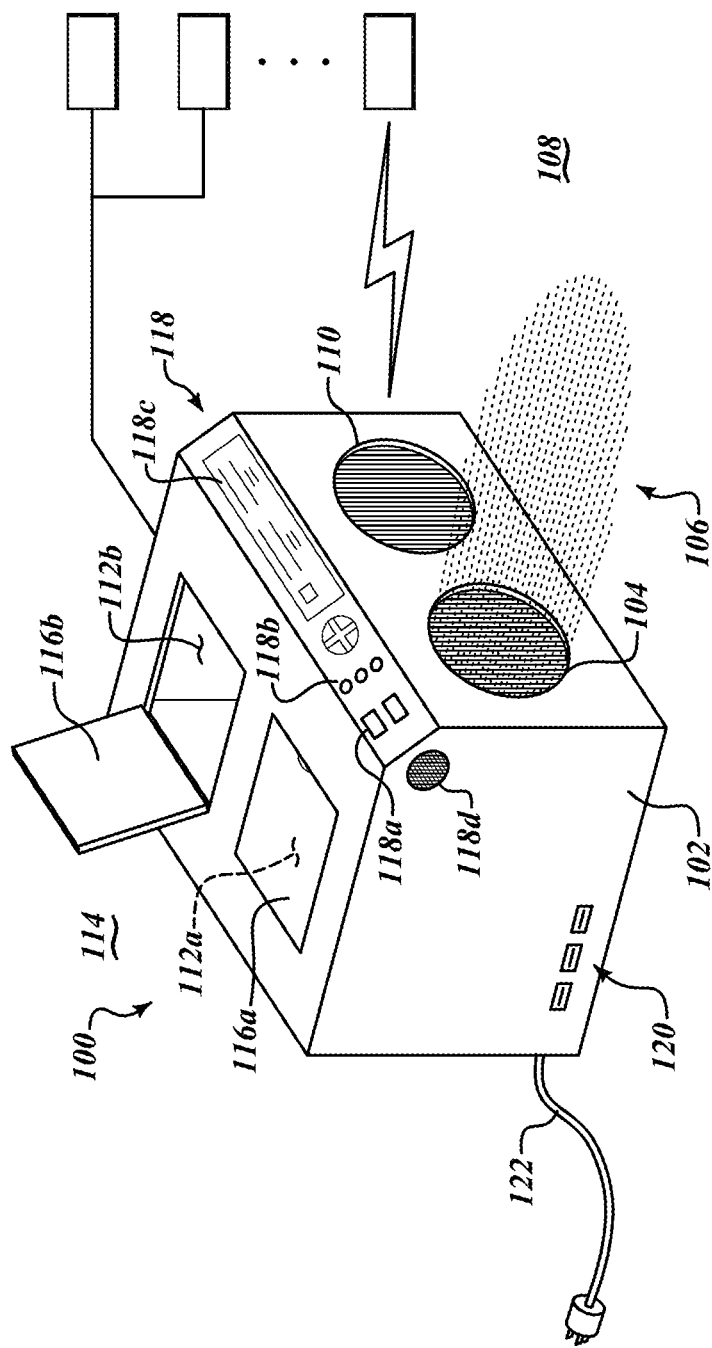
FIG. 1 is an isometric view of a disinfection system to disinfect or sterilize a room or other volume according to one illustrated embodiment, the disinfection system communicatively coupled to a number of external sensors.
Figure 2:
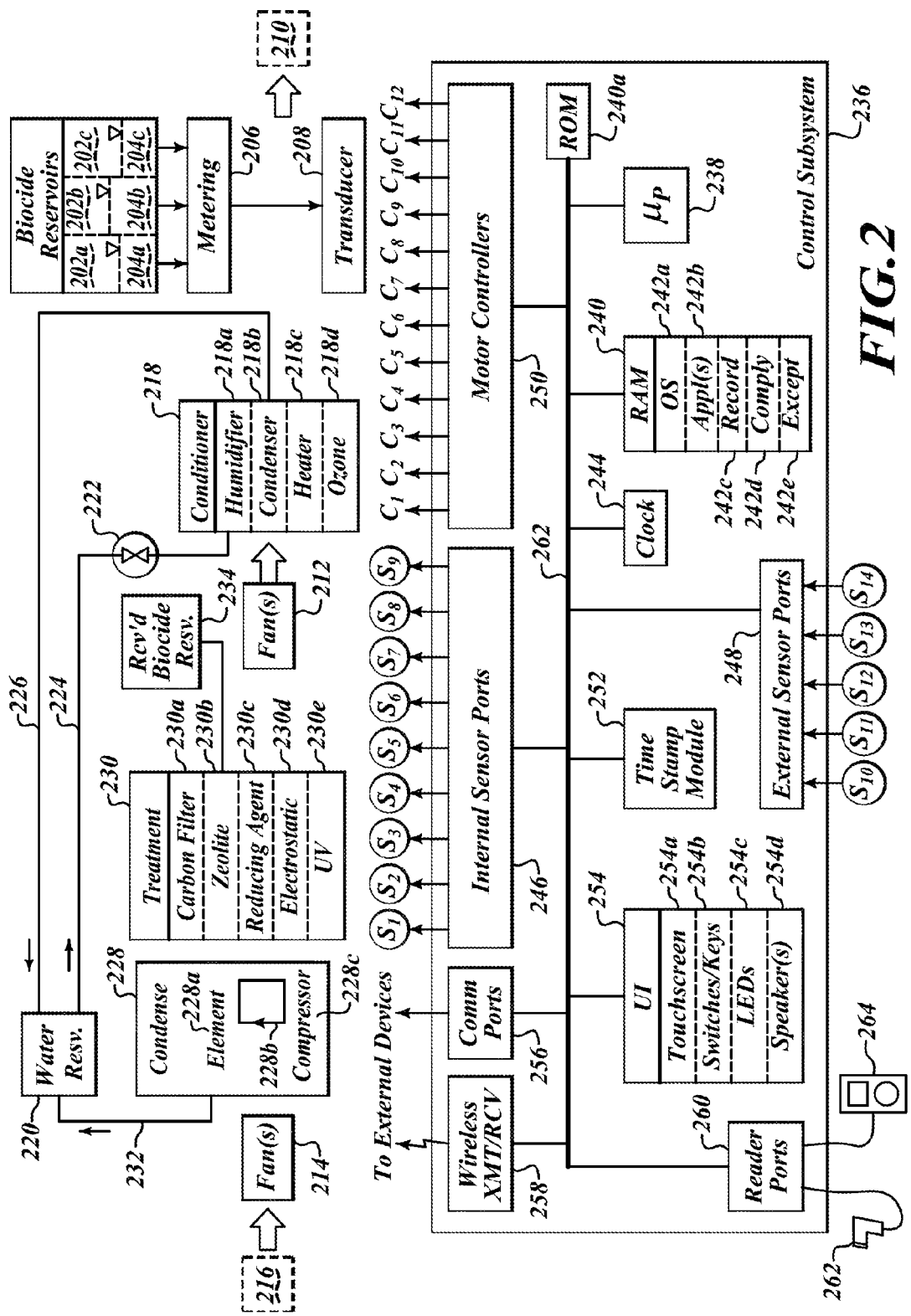
FIG. 2 is a schematic diagram of the disinfection system of FIG. 1 according to one illustrated embodiment, coupled to the external sensors.

FIGS. 1 and 2 show a disinfection system 100 according to one illustrated embodiment.

As explained in detail below, the disinfection system 100 may be operated to sterilize, disinfect or otherwise sanitize a space such as a room or other volume, including surfaces of the space and objects contained within the space. The disinfection system 100 may be used to sterilize, disinfect or otherwise sanitize spaces used in medical facilities or procedures, for instance surgery rooms or theaters, delivery rooms, examination rooms, patient rooms, wards, waiting areas, halls, and/or laboratories. Such may also be useful in other environments, such as public or private facilities in which people gather, reside or are confined or in which consumable products such as food or beverages are prepared, processed, or packaged. Such environments may, for example include sports arenas or stadiums, theaters, amusement parks, museums, exhibition halls, or convention centers. Such environments may, for example, include conveyances such as trains, ships, airplanes, buses, trucks, and associated facilities such as terminals, stations, waiting areas or rooms, loading docks, or warehouses. Such environments may, for example include apartment houses or blocks, public housing, hotels, motels, barracks, or camp bunkhouses. Such environments may, for example include jails, prisons or other detention facilities. Such environments may include kitchens, factories, and various food processing or packaging facilities. Such may also be useful in sanitizing vents or other spaces associated with heating, ventilation and air conditioning (HVAC) equipment and systems.

With reference to FIG. 1, the disinfection system 100 includes a housing 102, having an exhaust or outlet port 104 to exhaust a sterilizing, disinfecting or sanitizing medium 106 into an ambient environment 108 from the disinfection system 100. As described herein, the sterilizing, disinfecting or sanitizing medium 106 is exhausted in the form of a "dry fog" (i.e., a non-wetting mist that does not moisten surfaces exposed to the non-wetting mist). The disinfection system 100 may optionally include an extraction or inlet port 110 to extract or withdrawn at least some of the exhausted sterilizing, disinfecting or sanitizing medium or dry fog 106 from the ambient environment 108. While the illustrated embodiment includes separate exhaust and extraction ports 104, 110, respectively, some embodiments may employ the same port or ports for both exhaust and extraction of the sterilizing, disinfecting or sanitizing medium 106.

The disinfection system 100 may include a number of reservoirs 112a, 112b (collectively 112) designed to hold sterilizing, disinfecting or sanitizing medium, and optionally to hold water or some other medium. For example, the disinfection system 100 may include three reservoirs that may each selectively hold a respective one of three different disinfection agents (e.g., chlorine dioxide, peracetic acid, hydrogen peroxide, electrochemically activated solutions such as electrolyzed water). Such reservoirs 112 may, for example, hold biocide agent in a dry form, for instance prior to nebulization. Alternatively, or additionally, such reservoirs 112 may hold a biocide agent solution in a liquid form.

Also for example, the disinfection system 100 may additionally, or alternatively, include a reservoir to hold water. For example, a water holding reservoir may hold water to mix with a dry biocide agent to create a solution of biocide agent. Additionally or alternatively, a water holding reservoir may hold water extracted from the ambient environment and condensed therefrom. Also for example, the disinfection system 100 may additionally, or alternatively, include an extraction or recovery reservoir to hold material such as recovered biocide agent extracted from the environment. Also for example, the disinfection system 100 may additionally, or alternatively, include a reservoir to hold a neutralizing agent (e.g., decontaminate neutralizing agent). A neutralizing agent holding reservoir may hold one or more neutralizing agents or chemicals which may be dispersed from the disinfection system 100 to neutralize previously dispersed biocide agent or a byproduct of the previously dispersed biocide agent and material in the ambient environment. Such may, for example, neutralize a toxicity created by the previously dispersed biocide agent.

As illustrated, interiors of the reservoirs 112 may be accessible from an exterior 114 of the disinfection system 100 to allow the loading and/or unloading of media from the reservoirs 112. The disinfection 100 system may include covers 116a, 116b (collectively 116) selectively moveable between closed position (illustrated by cover 116a) and opened position (illustrated by cover 116b) to selectively provide and deny access to the interiors of the reservoirs 112 from the exterior of the disinfection system 100.

The disinfection system 100 may include a user interface, generally illustrated as 118, to allow an end user to operate or otherwise provide input to the disinfection system 100 and/or to provide output to the end user regarding the operational state or condition of the disinfection system. The user interface 118 may include a number of user actuatable controls accessible from the exterior of the disinfection system 100. For example, the user interface 118 may include a number of switches or keys 118a operable to turn the disinfection system ON and OFF and/or to set various operating parameters of the disinfection system. The user interface 118 may also include one or more visual indicators 118b, for instance light emitting diodes (LEDs). The visual indicators 118b may be single color or may be capable of producing different color indicia corresponding to various operational states or conditions of the disinfection system. Additionally, or alternatively, the disinfection system 100 may include a display, for instance a touch panel display 118c. The touch panel display 118c (e.g., LCD with touch sensitive overlay) may provide both an input and an output interface for the end user. The touch panel display 118c may present a graphical user interface, with various user selectable icons, menus, check boxes, dialog boxes, and other components and elements selectable by the end user to set operational states or conditions of the disinfection system 100. The user interface 118 may also include one or more auditory transducers 118d, for example one or more speakers and/or microphones. Such may allow audible alert notifications or signals to be provided to an end user. Such may additionally, or alternatively, allow an end user to provide audible commands or instructions. The user interface 118 may include additional components and/or different components than those illustrated or described, and/or may omit some components. The switches and keys 118a or the graphical user interface may, for example, include toggle switches, a keypad or keyboard, rocker switches, trackball, joystick or thumbstick. The switches and keys 118a or the graphical user interface may, for example, allow an end user to turn ON the disinfection system 100, start a sterilization, disinfection or sanitization cycle, adjust a level or concentration of a biocide agent dispersed, select from a number of biocide agents, select a sequence for dispersal of multiple biocide agents, select a duration of a sterilization, disinfection or sanitization cycle, adjust one or more frequencies of a nebulizer or transducer, select or adjust an output type (e.g., type of visual alert, type of aural alert) or level (e.g., brightness, sound level or volume, etc.).

The disinfection system 100 may include one or more communications ports 120 which may allow selective wired or wireless communicative connections or coupling to one or more external components. For example, wired or wireless communicative connections or couplings may be made to one or more external sensors 122. Additionally, or alternatively, wired or wireless communicative connections or couplings may be made to one or more networked, or non-networked, external devices such as computer systems, servers, bridges, and/or routers. Such may, for example, allow remote activation and/or control of the disinfection system 100. The disinfection system 100 may optionally include a power cord, which allows the disinfection system 100 to be powered by an external source of power, for instance a source of alternating current (AC) power such as a standard wall receptacle supplied via the power grid. Additionally, or alternatively, the disinfection system 100 may include one or more internal power sources (e.g., primary and/or secondary chemical batteries, super- or ultracapacitors, and/or fuel cells, not shown in FIG. 1).

With reference to FIG. 2, the disinfection system 100 may include a number of biocide reservoirs 202a-202c (three illustrated, collectively referenced as 202). As discussed above, there may be more than one biocide reservoir 202, which may be filed with respective biocide agents 204a-204c (collectively 204). Biocide agent 204 may, for example, be supplied as a liquid or a powder. Alternatively, biocide agent 204 may be supplied in other forms. In some embodiments, biocide reservoirs 202 may take the form of removable reservoirs, for example in the form of removable cartridges or canisters.

The disinfection system 100 may include one or more metering mechanisms 206 to meter biocide agent 204 from the biocide reservoirs 202 in a desired or defined amount. The metering mechanism(s) 206 may take a variety of forms, including a valve, a shaker or sifter, a conveyor, a jet, to name a few.

The disinfection system 100 may include one or more transducers 208 selectively operable to nebulizer the biocide agent. As used herein and in the claims the term nebulize and variations thereof (e.g., nebulizes, nebulization) mean the atomization or breaking up of a biocide agent into sufficiently fine particles so as to produce a fine spray or mist, for instance a "dry powder" fog which does not wet surfaces. In practice, the nebulizer may produce water droplets laden with a biocide agent (e.g., $ClO_2$ and/or $H_2O_2$). The droplets should be sufficiently fine as to not wet surfaces or objects such as sensitive electrical or electronic equipment.

The transducer(s) 208 may take a variety of forms, including one or more piezoelectric transducers, vibration table associated with one or more motors and/or one or more transmissions, oscillating or vibrating meshes/membranes, oscillating or vibrating magnets, jets and source of a compressed fluid to drive the jet, to name a few. Piezoelectric transducers typically are driven by a high frequency voltage source, and may mechanically impart its oscillatory or vibratory motion directly to the biocide agent or via some intermediary structure. Jet nebulizers, sometimes referred to as atomizers, typically employ a jet port which emits a fluid (e.g., air or oxygen) at a high velocity, and possibly with significant turbulence, into the substance (e.g., biocide) to be delivered. The fluid is supplied to the jet port at an elevated pressure relative to the ambient pressure, typically via conduit, valves and a compressor.

The transducer(s) 208 may, for example, be used to break up a biocide agent solution or suspension to produce an aerosol (i.e., mixture of gas and particle), for exhaustion into the ambient environment as part of an exhaust stream. An aerosol may take a variety of forms. For example, an aerosol may take the form of vaporized water entrained in warm air, which produces a mist.

The transducer(s) 208 may vibrate or oscillate or produce vibration or oscillation at one or more desired or defined frequencies. For example the transducer(s) 208 may vibrate at one or more ultrasonic frequencies to obtain sufficiently nebulization to achieve distribution as a dry powder fog 210. The defined frequency or frequencies may be specifically selected for the particular biocide agent, for example based on empirical studies.

The disinfection system 100 may include one or more fans. For example, the disinfection system 100 may include one or more exhaust fans 212 positioned and operable to exhaust the nebulized biocide agent from the disinfection system 100 as a dry fog 210, for example via the exhaust port 104 (FIG. 1). The exhaust fan(s) 212 may ensure adequate dispersal or coverage of the room or space being subjected to the sterilization, disinfection or sanitization. Also for example, the disinfection system 100 may include one or more extraction fans 214 positioned and operable to extract or withdraw the nebulized biocide agent or dry fog 216 from the ambient environment, for example via the extraction or input port 110 (FIG. 1).

On the exhaustion or distribution side, the disinfection system 100 may include a conditioning subsystem 218 operable to condition air, water or the resultant exhaust stream or dry fog. Conditioning of air prior to exhaustion into the ambient environment may allow for quicker, more complete dispersal of biocide into the ambient environment. The conditioning subsystem 218 may include one or more distinct conditioning elements. For example, conditioning subsystem 218 may include a humidifier 218a selectively operable to humidify air. The humidifier 218a may be fluidly coupled to receive a fluid, such as water, from a fluid reservoir 220, for example via a valve 222 and conduit 224. The fluid in the fluid reservoir 220 or supplied therefrom may undergo conditioning, such as being filtered, demineralized and/or subjected to UV light. Alternatively, or additionally, the conditioning subsystem 218 may, for example, include a condenser 218b, for instance with a refrigerated coil. The condenser 218b may, for example include a condensation element (e.g., condenser coil, not shown), which carries a thermal transfer medium (e.g., refrigerant or coolant, not shown), and a compressor (not shown) coupled to adjust a pressure of the thermal transfer medium. The condenser 281b may be fluidly communicatively coupled to provide condensed fluid to the fluid reservoir 220, for example via conduit 226. The humidifier 218a may be used to humidify air as part of exhausting biocide agent(s) to the ambient environment. Additionally, or alternatively, the humidifier 218a may be used to return the ambient environment to a desired or define relative humidity after the dry fog or biocide agent is extracted, evacuated or withdrawn from the ambient environment.

Alternatively, or additionally, the conditioning subsystem 218 may, for example, include a heater 218c. The heater 218c may take a variety of forms, for example a resistive element or coil which produces radiant and/or convective heat when a current is passed therethrough. Alternatively, or additionally, the conditioning subsystem 218 may, for example, include a ozone generator 218d. The ozone generator 218d may take a variety of forms, for example a corona discharge ozone generator or an ultraviolet light based ozone generator. Suitable filters for filtering air, fluid and/or the exhaust stream may be positioned at various locations throughout the disinfection system.

On the extraction or withdrawal side, the disinfection system 100 may include a condenser 228 and/or treatment subsystem 230. The condenser 228 may, for example include a condensation element 228a (e.g., condenser coil), which carries a thermal transfer medium 228b (e.g., refrigerant or coolant), and a compressor 228c coupled to adjust a pressure of the thermal transfer medium 228b. The condenser 228 may be fluidly communicatively coupled to provide condensed fluid to the fluid reservoir 220, for example via a conduit 232. The condenser 228 may be used to remove vapor form dry fog extracted from the ambient environment. Additionally, or alternatively, the condenser 228 may be used to return the ambient environment to a desired or define relative humidity after the dry fog or biocide agent is extracted, evacuated or withdrawn from the ambient environment.

The treatment subsystem 230 may be used to scour or filter the extraction stream (e.g., dry fog) and/or treat biocide agent extracted or withdrawn from the ambient environment. The treatment subsystem 230 may take a variety of forms, and may include a number of different elements each capable of treating the withdrawn biocide in a respective manner. For example, the treatment subsystem 230 may include one or more activated carbon filters and/or HEPA filters 230a. Filters may include crystals or a catalytic-type filter such as a platinum or a silver catalyst. Additionally, or alternatively, the treatment subsystem 230 may include one or more structures or beds of Zeolite 230b. One or more filters may be removable and replaceable. Additionally, or alternatively, the treatment subsystem 230 may include one or more reducing agents 230c. Additionally, or alternatively, the treatment subsystem 230 may include one or more electrostatic treatment systems 230d operable to electrostatically charge biocide agent and thereby remove the biocide agent from the extraction stream. Additionally, or alternatively, the treatment subsystem 230 may include one or more UV treatment systems 230e selectively operable to expose the recovered biocide agent to UV light of particular wavelengths and/or intensities. Recovered biocide agent may be provided to an extracted or received biocide agent reservoir 234 in treated or non-treated condition. In some embodiments, extracted or recovered biocide agent may be returned directly to the biocide reservoirs 202, treated or untreated, for reuse. Suitable filters for filtering air, fluid and/or the extraction stream may be positioned at various locations throughout the disinfection system.

The disinfection system 100 may include a control subsystem 236. While an exemplary control subsystem 236 is illustrated and described, one or ordinary skill in the art will appreciate that other control subsystem 236 architectures and elements may be employed.

The control subsystem 236 includes a controller 238, for example a microprocessor, digital signal processor, programmable gate array (PGA) or application specific integrated circuit (ASIC). The control subsystem 236 include one or more non-transitory storage mediums, for example read only memory (ROM) 240a, random access memory (RAM) 240b, Flash memory (not shown), or other physical computer- or processor-readable storage media (collectively 240). The non-transitory storage mediums 240 may store instructions and/or data used by the controller 238, for example an operating system (OS) 242a and/or applications 242b. The instructions as executed by the controller 238 may implement a recording module 242c to record various parameters, a compliance reporting module 242d to produce reports such as compliance reports, and an exception reporting module 242e to handle exceptions (e.g., failures, out of compliance issues or variations from expected operation or thresholds). The control subsystem 236 may also include one or more clocks 244, which may allow determination of real world dates and time. Such may be useful for operating or synchronizing with a scheduling system, as discussed below. Such may additionally, or alternatively, be useful in stopping the exhausting of biocide agent to the ambient environment after a first defined period, stopping the extraction of biocide agent from the ambient environment after a second defined period and/or turning the disinfection system OFF or enter a low energy consumption sleep mode after a third defined period to reduce power consumption.

The control subsystem 236 may be programmed to operate according to a schedule, for example based on a real time clock. Alternatively, or additionally, the control subsystem 236 may be operated remotely via a handheld remote control transceiver or via a computer communicatively coupled to the control system via one or more wired or wireless channels.

The control subsystem 236 may include one or more internal sensors, represented in FIG. 2 as circles with respective identifiers ($S_1$-$S_9$), positioned, configured and operable to sense various operation characteristics of the various elements or components of the disinfection system 100. The internal sensors $S_1$-$S_9$ are communicatively coupled via one or more internal sensor ports 246 to provide signals indicative of such to a controller 238 such as a microprocessor. For clarity of illustration, the internal sensors $S_1$-$S_9$ are all grouped together proximate the other elements of the control subsystem 236. In practice, these internal sensors $S_1$-$S_9$ will typically be located proximate the various elements or components which the internal sensors $S_1$-$S_9$ are monitoring. The denomination internal is used to indicate that the sensors $S_1$-$S_9$ are part of the disinfection system 100 and typically housed therein, and to distinguish such from external sensors, discussed below.

The internal sensors $S_1$-$S_9$ may, for example, include one or more biocide agent reservoir sensors $S_1$ to sense or monitor a quantity (e.g., volume or level) of biocide agent in the biocide agent reservoir(s) 202. Such may assure that biocide agent reservoir levels were adequate during a sterilization, disinfection or sanitation cycle, and/or may allow notification when biocide reservoirs 202 require refilling.

The internal sensors may include a fluid reservoir sensor $S_2$ to sense or monitor a quantity (e.g., volume or level) of fluid in the fluid reservoir 220. Such may assure that fluid reservoir level is adequate during a sterilization, disinfection or sanitation cycle, and/or may allow notification when the fluid reservoir 220 requires refilling or emptying.

The internal sensors may include one or more temperature sensors $S_3$ to sense monitor temperature at one or more locations, for instance, temperature of the heater 218c or proximate heater 218c such as in the exhaust or output stream of dry fog 210. Such may allow feedback control of the heater 218c and/or assure that a temperature is adequate during a sterilization, disinfection or sanitation cycle.

The internal sensors may include one or more valve sensors $S_4$ to sense or monitor a state or position of one or more valves, for instance the valve 222. Such may allow feedback control of the valve 222 and/or assure that sufficiently fluid is provided during a sterilization, disinfection or sanitation cycle.

The internal sensors may include one or more fan sensors $S_5$ to sense or monitor a state or speed of one or more fans, for instance the exhaust fans 212. The internal sensors may include one or more fan sensors $S_6$ to sense or monitor a state or speed of one or more fans, for instance extraction fans 214. Such may allow feedback control of the fans 212, 214 and/or assure that a flow rate is adequate during a sterilization, disinfection or sanitation cycle.

The internal sensors may include one or more transducer sensors $S_7$ to sensor or monitor a state or frequency of oscillation or vibration of one or more transducers, for instance the transducer 208. Such may allow feedback control of the transducer 208 and/or assure that oscillation or vibration is adequate to achieve the desired or defined level of nebulization during a sterilization, disinfection or sanitation cycle.

The internal sensors may include one or more meter sensors $S_8$ to sense or monitor a state or condition of one or more metering mechanisms, for instance flow rate. Such may allow feedback control of the metering mechanism 206 and/or assure that a desired or defined amount or quantity of biocide agent was provided to the transducer 208 during a sterilization, disinfection or sanitation cycle.

The internal sensors may include one or more exhaust concentration sensors $S_9$ to sense or monitor a concentration of biocide agent in the dry fog stream being exhausted from the disinfection system 100. Such may allow feedback control of the various elements or components of the disinfection system 100 and/or assure that adequate concentrations of biocide agent were dispersed during a sterilization, disinfection or sanitation cycle.

The disinfection system 100 may include additional internal sensors and/or may omit some of the internal sensors discussed above. For example, the disinfection system 100 may include additional internal sensors to detect one or more characteristics of material extracted or recovered from the ambient environment. Such sensor(s) may, for instance, be associated with an extraction or recovery reservoir. For example, sensors may be used to determine a quantity or amount of material extracted or recovered, as well as physical or chemical properties thereof, such as pH level. Such may indicate whether the extracted or recovered material is safe to dispose of, or whether such is safe for reuse. As discussed below, various sensor readings or measurements may be employed in compliance reporting and/or exception reporting. A variety of parameters may be monitored, of a variety of substances, for example the preparation to be nebulized may be monitored, the collected de-humidified liquid may be monitored for example to ensure it is safe for disposal and to establish how much has been recovered, and how much residual active agent may remain in the fogged space, and/or the active agent may be monitored. The environment may be monitored during fogging and after to establish levels of hazard. The bactericidal strength of the preparation may be monitored; the amount delivered into the area to be decontaminated or otherwise treated may be monitored, as may the time the solution remains in contact with the area.

The control subsystem 236 may include one or more external sensors, represented in FIG. 2 as circles with respective identifiers $S_{10}$-$S_{14}$, positioned, configured and operable to sense various operation characteristics of the various elements or components of the disinfection system 100. The external sensors $S_{10}$-$S_{14}$ are communicatively coupled via one or more external sensor ports to provide signals indicative of such to a controller such as the microprocessor. The communicative coupling may be wired (e.g., electrical, optical fiber) or wireless (e.g., radio in the radio or microwave wavelengths, light including infrared). For clarity of illustration, the external sensors $S_{10}$-$S_{14}$ are all grouped together proximate the other elements of the control subsystem 236. In practice, these external sensors $S_{10}$-$S_{14}$ will typically be located in the ambient environment proximate areas which the external sensors $S_{10}$-$S_{14}$ are monitoring. The denomination external is used to indicate that the sensors $S_{10}$-$S_{14}$ are external from the disinfection system 100 and typically housed outside of such, and to distinguish such from internal sensors $S_1$-$S_9$, discussed above.

The external sensors may, for example, include one or more ambient environment concentration sensors $S_{10}$ to sense an amount, density or concentration of fog and/or biocide agent in the ambient environment. Such may allow feedback control of the various elements or components of the disinfection system 100 and/or assure that adequate concentrations of biocide agent were dispersed during a sterilization, disinfection or sanitation cycle.

The external sensors may include one or more ambient environment presence sensors $S_{11}$ to sense or monitor a presence of biocide agent in the ambient environment. Such may allow feedback control of the various elements or components of the disinfection system 100 and/or assure that adequate concentrations of biocide agent were dispersed during a sterilization, disinfection or sanitation cycle.

The external sensors may include one or more wetness sensors $S_{12}$ to sense or monitor a wetness of surface(s) in the ambient environment. The external sensors may include one or relative humidity sensors $S_{13}$ to sense or monitor a relative humidity in the ambient environment. Such may allow feedback control of the various elements or components of the disinfection system 100 and/or assure that adequate concentrations of biocide agent were dispersed during a sterilization, disinfection or sanitation cycle.

The external sensors may include one or more temperature sensors $S_{14}$ to sense monitor temperature at one or more locations in the ambient environment. Such may allow feedback control of the various elements or components of the disinfection system 100 and/or assure that the ambient environment was at a suitable desired or defined temperature during a sterilization, disinfection or sanitation cycle.

Fog or biocide concentration, wetness, relative humidity, temperature and/or time, alone or in combination may provide an indication of the distribution and/or effectiveness of the biocide agent dispersal. For example, exposure of surfaces or ambient air to certain concentrations of selected biocide agents for defined durations at defined temperatures may assure effective sterilization, disinfection or sanitization, and may meet some required or desired standard to assure compliance with specific hospital, industry, governmental or insurer set guidelines. The disinfection system 100 may include additional external sensors and/or may omit some of the external sensors discussed above. The external sensors $S_{10}$-$S_{14}$ may be positioned at one or more locations throughout a room or space. As discussed below, various sensor readings or measurements may be employed in compliance reporting and/or exception reporting, for example reporting on fog concentration measured or sensed at one or more locations in a room.

The control subsystem 236 may include one or more motor controllers 250 communicatively coupled to control one or more elements of the disinfection system. The motor controller(s) 250 may operate in conjunction with a controller 238, such as a microprocessor, typically based on sensed conditions and programmed logic, to provide control signals $C_1$-$C_{12}$ to control motors, solenoids, valves and/or other actuators. For clarity of illustration, the motor control signals $C_1$-$C_{12}$ all grouped together proximate the other elements of the control subsystem 236. In practice, these signals are coupled to motors, solenoids and other actuators typically located throughout the disinfection system 100 and typically housed therein.

For example, on the exhaust side, the motor controller(s) may provide control signals $C_1$ to control the metering mechanism 206 to meter or otherwise provide desired or defined amounts of biocide agents 204 from the biocide agent reservoir(s) 202 to the transducer 208.

The motor controller(s) may provide control signals $C_2$ to control one or more fans, for example to control a state or speed of exhaust fan(s) 212. The motor controller(s) may provide control signals $C_3$ to control one or more fans, for example to control a state or speed of extraction fan(s) 214. As noted above, the disinfection system 100 may employ the same fan or fans to both exhaust biocide agent into the ambient environment and extract biocide agent therefrom. In such embodiments, the control signals $C_2$ may cause the fan to operate (e.g., rotate) in a first direction (e.g., clockwise) when exhausting, and operate in a second, opposite direction (e.g., counterclockwise) when extracting.

The motor controller(s) may provide control signals $C_4$ to control one or more transducers 208, for instance controlling a state or frequency of oscillation or vibration of the transducer 208. The control signals $C_4$ may be a relatively simple sinusoidal fluctuating voltage or current, or may be more complex. For example the control signals $C_4$ may employ multiple complex wave forms. The control signals $C_4$ cause the transducer to vibrate or oscillate at a number of respective frequencies, specifically selected to achieve a desired level of nebulization of the particular biocide agent 204. The control signals $C_4$ may take the form of analog signals or digital signals. The control signals $C_4$ may take the form of pulse width modulated signals.

The motor controller(s) may provide control signals $C_5$ to control the humidifier 218*a*. The control signals $C_5$ may cause the humidifier to humidify air to a achieve a desired relative humidity prior to exhaustion of same into the ambient environment via the exhaust or output port 104 (FIG. 1).

The motor controller(s) may provide control signals $C_6$ to control one or more valves, for example to control the valve 222 to regulate a flow of fluid (e.g., water) from the fluid reservoir 220. Such may, for instance, regulate a flow of fluid to the humidifier 218*a*.

The motor controller(s) may provide control signals $C_7$ to control one or more condensers 218*b* of the conditioning subsystem 218, for instance controlling operation of a compressor thereof. The control signals $C_7$ may cause the condenser to condense water vapor from air to achieve a desired level of relative humidity prior to exhaustion of same into the ambient environment via the exhaust or output port 104 (FIG. 1).

The motor controller(s) may provide control signals $C_8$ to control one or more heaters, for instance to control the heater 218c. The control signals $C_8$ may cause the heater 218c to adjust a temperature of air to a desired or defined temperature prior to exhaustion of same into the ambient environment via the exhaust or output port 104 (FIG. 1).

The motor controller(s) may provide signals $C_9$ to control operation of the ozone generator 218d. For example, the control signals $C_9$ may control the zone generator 218d to generate ozone for inclusion in the exhaust stream prior to exhaustion of same into the ambient environment via the exhaust or output port 104 (FIG. 1).

For example, on the extraction or withdrawal side, the motor controller(s) may provide control signals $C_{10}$ to control a compressor 228c associated with a condenser 228. Such may, for example, condense water vapor from dry fog extracted from the ambient environment, for instance via extraction or intake port 110 (FIG. 1).

The motor controller(s) may provide control signals $C_{11}$ to control an electrostatic discharge element 230d of the treatment subsystem 230. For example the control signals $C_{11}$ may cause the electrostatic discharge element 230d to electrostatically charge extracted biocide agent, to extract such from the extraction stream.

The motor controller(s) may provide control signals $C_{12}$ to control one or more UV elements 230*e*. For example, control signals $C_{12}$ may control one or more UV elements 230*e* to expose the extracted biocide agent to desired or defined wavelengths and intensities of UV light.

The control subsystem 236 may optionally include a time stamp module 252. The time stamp module 252 provides unalterable time stamping (i.e., date and time) for various parameters or system operations. The time stamp module 252 may be configured to operate with the controller 238, such as a microprocessor, to time stamp when certain operational activities have been performed and/or when certain sensor measurements or readings occurred. As explained below, such may allow independent verification that the disinfection system 100 is operating properly and that the end user is operating and/or maintaining the disinfection system 100 correctly and timely. The time stamp module 252 may be a third party module, and may include a self contained clock. The time stamp module 252 should be tamper-resistant such that any attempts to tamper with such are deterred, and identifiable. For example, the time stamp module 252 may be designed such that attempts to tamper with the time stamp module 252 destroys the time stamp module 252 or renders such incapable of further operation.

As previously noted, the control subsystem 236 may include a user interface 254, for example including a touch screen display 254*a*, switches or keys 254*b*, visual indicators (e.g., LEDs) 254*c* and/or speaker(s) 254*d*.

The control subsystem 236 may include a number of communications ports to provide wired (e.g., electrical or optical fiber) or wireless (e.g., radio including radio and microwave frequencies, light including visible or infrared) communications. For example, the control subsystem 236 may include one or more wired ports 256 to provide wired communications with external devices such as computers, server computers, networks, and/or other disinfection systems. Such wired ports 256 may conform to any of a large variety of existing specifications and protocols (e.g., RJ-11, USB, FIREWIRE®, Ethernet). The control subsystem 236 may include one or more wireless ports 258 including transmitters, receivers or transceivers and/or antennas. Such wireless ports 258 may conform to any of a large variety of existing specifications and protocols (e.g., 802.11, BLUETOOTH®, WI-FI, MI-FI). Such may allow uni- or bi-directional communications, for instance uni-cast, multi-cast or broadcast communications.

The control subsystem 236 may include one or more reader ports 260 to communicatively couple with one or more automatic data collection readers 262, 264. The automatic data collection readers 262, 264 are dedicated to reading and/or writing data to one or more data carriers such as machine-readable symbols (not shown) and RFID transponders or tags (not shown). The automatic data collection readers 262 264 may, for example, take the form of, or include, a machine-readable symbol reader 262, for instance a scanner or imager capability of optically reading machine-readable symbols (e.g., barcode, area or matrix code or stacked code symbols). Also for example, the automatic data collection readers 262, 264 may take the form of, or include, an RFID reader 264, for instance an RFID interrogator capability of wirelessly reading information from an RFID data carrier such as an RFID transponder or tag. The automatic data collection readers 262, 264 may combine machine-readable symbol and RFID reading capabilities. Suitable dedicated automatic data collection readers 262, 264 may be commercially available from Intermec Technologies or Symbol Technologies. Additionally, or alternatively, the dedicated automatic data collection readers 262, 264 may be capable of reading or writing to other data carriers such as optical memories, touch memories (e.g., available from Dallas Semiconductor), magnetic stripes, etc.

The data carriers may take a large variety of forms, including but not limited to labels or tags that carry machine-readable symbols or that otherwise encode machine-readable information (e.g., RFID, optical memories, touch memories, magnetic stripes). The data carrier may advantageously encode information in two or more forms, for example an RFID transponder that carries or bears a machine-readable symbol.

The automatic data collection readers 262, 264 may include one or more processors and/or memory (not illustrated). The automatic data collection readers 262, 264 may be configured to process or pre-process information read from the data carrier. For example, the automatic data collection readers 262, 264 may be configured to automatically recognize symbols from various symbologies and decode the same. The automatic data collection readers 262, 264 may be configured to write data to a data carrier. For example, the dedicated automatic data collection reader 264 may be configured to automatically write information to an RFID data carrier.

The automatic data collection readers 262, 264 may be employed to read information from data carriers physically associated with a room or space, a person such as an end user, patient and/or one or more medical care providers (e.g., doctors, nurses, anesthesiologist, radiology technician), for instance from a data carrier of a wrist band 2922*c*, anklet or badge worn by the end user, patient or medical care provider, and/or various objects (e.g., implements, tools, machines including the disinfection system, devices, sponges, pads, gauze, articles and/or other supplies). Such can be integrated with other automatically collected information, such as information indicative of a condition of the disinfection system 100 and operation thereof, as well as sensed parameters from throughout the ambient environment which is being subjected to a sterilization, disinfection or sanitization process during a sterilization, disinfection or sanitization cycle.

Information read from a data carrier may, for example include an identifier, such as a unique identifier that uniquely identifies the RFID transponder or tag, disinfection system, end user or room. A database stored on a non-transitory computer-readable storage medium may associate the identifier with information that identifies the object to which the RFID transponder or tag is attached, as well as information about the object. The information may include identity of the object such as manufacturer, model, type, classification, lot number and/or date of manufacture of the disinfection system, the biocide agents in the reservoirs thereof, the name or other identifier of the medical facility and room identifier, and/or a name or unique identifier of an end user operator of the disinfection system. The information may include a history of the disinfection system, for instance number of uses, number and/or type of sterilization cycles, number and/or date of refurbishment, dates and/or times of use, dates of inspection and/or identity of inspector, identity of end user operator, dates and times of disinfection cycles.

The control subsystem 236 may include one or more busses 262 (only one illustrated for sake of clarity) or other structures to communicatively couple the various elements or structures of the control subsystem 236. Such may include one or more power buses, instruction buses, data busses or other buses or communicative structures.

While not illustrated the disinfection system 100 may include a delivery duct in the form of a flexible hose, which may be used to manually direct the cloud or dry fog to particular areas which may be considered difficult to access, and which are therefore potential repositories of pathogens and infection, and for which it is desired that particular care be taken. The delivery duct may, for example, have a length of greater than 2 meters, between 1 meter and 2 meters, or even up to 1 meter. The delivery duct may provide a convoluted or circuitous flow path, and may be serpentine or zigzag. This internal structure of the delivery duct may provide a path structured to assist in deterring particles of an undesirably large size to exit the duct.

The delivery duct length may be varied, for example to selectively reduce the number of larger droplets exiting the duct. It is contemplated that a delivery duct length of at least one meter is required to discourage droplets with a diameter greater than the desired, predetermined size to exit the duct. A longer duct allows a higher proportion of droplets of a still smaller diameter to enter the room or space to be treated. Limiting the droplet size affects the dryness of the fog containing the droplets, for example if a substantial portion of the droplets, perhaps substantially 90% or more of the droplets, have a droplet diameter of less than the predetermined size, for example but not limited to 6.31 micrometers diameter, a much dryer fog than that produced by prior art systems is created. In addition a more consistent droplet size may be produced.

A piezoelectric ultrasonic nebulizer with a nebulizing transducer may be used to produce a fog of droplets from a reservoir of liquid. In general, ultrasonic foggers may employ a piezoelectric transducer with a resonating frequency of, 15 for example, around 1 to 2 MHz, more particularly 1.4 to 1.8 MHz, even more particularly for example 1.6 MHz. The delivery rate of fog produced can be adjusted by varying this frequency, and this can be accomplished by manually or automatically adjusting the voltage.

The disinfection system 100 may employ a number of individual nebulizing transducers (e.g., 8-24 distinct or separate nebulizing transducers) to act on a reservoir 212 of liquid, thereby producing a cloud of droplets in which substantially 90% of the droplets have a diameter of less than 6.31 µm (Sauter value). The droplets may be urged out of the disinfection system 100 by fan 212 and into a delivery duct. A length of the delivery duct may be varied, for example to selectively reduce the number of larger droplets exiting the duct. It is contemplated that a delivery duct length of at least one meter may be advantageously employed to discourage undesirably sized droplets (i.e., droplets with a diameter greater than 6.31 µm (Sauter value)) to exit the duct. A longer duct may produce droplets of a still smaller diameter for entry into the room or space to be treated. Limiting the droplet size such that substantially 90% or more of the droplets have a droplet diameter of less than 6.31 µm (Sauter value) results in a much dryer fog than that produced by conventional systems. The sizes may fall within the range of 1-8 micrometers diameter, or within the range of 1-7 micrometers diameter, or within the range of 1-6, 1-5, 1-4, 1-3, or even 1-2 micrometers diameter. For the purposes of this arrangement between 50-100% of the droplets are less than the above identified size. It is contemplated in particular that droplets may have a diameter 6.31 µm or less. More particularly it is contemplated that between 70% and 95% of the droplets have a diameter of the above identified size or less, still more particularly between 80 and 90% of the droplets have a diameter of the above identified size or less, more particularly still in which substantially 90% of the droplets have a diameter of the above identified size or less. This above identified size may advantageously be of the order of 6.31 µm diameter.

In some instances the biocide agent may be nebulized to obtain a particle or particulate size within the range of 1-8 micrometers, 1-6 micrometers, 1-4 micrometers or even 1-2 micrometers. In some instances, at least fifty percent of the particles delivered are less than the above identified size, in accordance with Dn(50), at least seventy percent of the particles delivered are less than the above identified size in accordance with Dn(70), or even at least ninety percent of the particles delivered are less than the above identified size in accordance with Dn(90). In some instances at least 70% of the particles are of the above identified size or less, at least 80% of the particles are of the identified size or less, or at least 90% of the particles are of the above identified size or less. Exposure to biocide agent may, for example, persist for 120 minutes or less, 90 minutes or less, 60 minutes or less, 30 minutes or less, 25 minutes or less, 20 minutes or less, 15 minutes or less, 10 minutes or less, or is even 5 minutes or less.

The speed at which any fan operates, indicating the energy imparted to droplets by means of the fan, also influences the number and size of particles delivered, and the rate of delivery of the fog. For example a gentle fan with a low fan speed, imparting little energy, will not provide heavier droplets with sufficient energy to escape the delivery duct so that lighter droplets will predominate, the heavier droplets falling back to the reservoir. A faster fan, imparting more energy, will provide more of the heavier droplets with sufficient energy to escape the delivery duct and so more heavier droplets will be present in the fog. The size and distribution of droplets generated by the present method therefore depends, at least in part, on the fan speed.

A fan (not shown) may also be positioned outside the device to drive the fog in a desired direction in a space to be treated. This might be particularly useful in unusually-shaped spaces, for example a corridor or such like.

A distal end of the delivery duct may include an internal lip (not shown). The cloud of nebulized particles escaping the duct may behave in many ways like a fluid. A fastest part of a fluid stream is typically the central portion, thus the internal lip may act to narrow the aperture and ensure only the fastest moving particles, which are likely to include the smallest and lightest particles, escape the duct. Additionally, the lip may provide a barrier for any liquid formed on the internal surface of the duct and urged towards the aperture by fan 212. During the nebulizing process set out herein, droplets produced from a nebulized sanitizing liquid each contain a significant proportion of the original disinfectant strength and each droplet will, on contact with a pathogen, deliver the active agent to the membrane of the pathogen. The interaction between disinfectant and pathogen renders the pathogen biologically inactive and kills the pathogen. The droplet may become neutralized once the active agent has been delivered.

This may be an effective method of destroying pathogens present in the air in the present and present in the disinfection system 100 itself. Pathogens present on surfaces may be rendered biologically inactive on contact with a droplet of the nebulized fog, however, the larger droplets of conventional approaches tend to settle on surfaces during condensation or following contact and this can result in the formation of a film of liquid on the surface. Such a liquid film can create a barrier between the active ingredient and any particle, for example a pathogen particle, on the surface, in particular if the biocide agent has been delivered rendering component droplets ineffective. Such larger droplets cannot access smaller crevices, and may even block access to smaller crevices. A repository of pathogen or infection may therefore be created or remain, which conventional systems cannot eradicate. In addition larger droplets tend to fall to the floor, or can be absorbed or remain on surfaces, causing such surfaces to become damp, wet and potentially damaged.

Droplets of a diameter less than 6.31 μm (Sauter value) retain their integrity more strongly than larger droplets and so, while droplets in the cloud touch all surfaces there is minimal coagulation and wetting. Any pathogen on a touched surface will be rendered inactive by action of the sanitizer or biocide in a droplet, however such droplets will form only a layer of micro-condensation which is negligible and transient, and does not form a barrier to the action of further droplets. As a consequence further droplets may interact with pathogens on the surface, rendering the pathogens biologically inactive. In addition, treated areas are lightly damped rather than wetted by exposure to the cloud of fog. Any light dampness dries out over a negligible time period leaving a treated room or space and its contents usable within a shorter period of time compared to known methods.

The smaller droplets produced by the disinfection system 100 taught herein are so light that, once the droplets exit the disinfection system 100, the droplets remain suspended in the air for several minutes without significant velocity. One measure of droplet density is the reduction in visibility, and in the present system a target visibility indicating sufficient density is between 0.5 and 2 meters, for example around one meter. The present method and system may also produce an appropriately uniform droplet density due to a broadly homogenous droplet distribution and this is apparent due to the lack of visible stratification of the droplet cloud. Stratification of fogged clouds is common in conventional systems; however the present system has particles which, due to their small size, are not inclined to coagulate and form larger heavier droplets which fall to the floor to cause wetting and stratification.

The effect of a fan on the size of droplets delivered following nebulization has been investigated by passing a laser light through fog produced during nebulization and measuring how much the beam is diffracted. Large droplets diffract the laser light less than small droplets and software can then calculate the size of droplets produced.

The spread of droplet size is set out in Table 1. Table 1 shows the effect on particle diameter of full, half and negligible fan speeds.

TABLE 1

Malvern Spraytec results for water droplets produced by the Contronics HU-85 apparatus

| Fan Speed | Time period measured | Dn(10) μm | Dn(50) μm | Dn(90) μm | Dv(10) μm | Dv(50) μm | Dv(90) μm | Sauter Mean μm |
|---|---|---|---|---|---|---|---|---|
| Full | 3 m 5 s | 1.58 | 3.14 | 5.41 | 3.43 | 7.92 | 17.96 | 6.50 |
| Half | 2 m 31 s | 1.85 | 2.93 | 6.31 | 3.27 | 7.53 | 16.49 | 6.16 |
| Effectively nil | 1 m 09 s | 2.15 | 3.41 | 5.41 | 2.68 | 4.29 | 6.44 | 3.96 |
| Effectively nil | 1 m 05 s | 2.15 | 2.93 | 5.41 | 2.83 | 4.19 | 8.31 | 4.48 |

The Dn(x) figures represent the diameter of a particle under which x % of the number of particles lie. For example, 10% of the particles will have a diameter under the figure for the Dn(10) i.e. in a group of 100 particle, 10 would have a diameter under the value for Dn(10). The Dv(x) is the diameter of a particle under which x % of the total volume of liquid lies. For example, if in all of the droplets measured there is a total of 100 cm$^3$ of liquid, the Dv(10) would be the upper bounding diameter of the first 10 cm$^3$ of droplets (placed in order of diameter) irrespective of how many individual droplets there are in that group. The Sauter mean is a value taking both volume and surface-area into account. It is used in cases where both volume and surface-area of the droplets is important, such as combustion or evaporation processes.

The Sauter mean values (shown in table 1) show a clear reduction, with decreasing fan speed, in droplet diameter where both surface-area and volume are taken in to account, from 6.5 μm to 4 μm. As can be seen, with no fan a fog can be produced with a Sauter mean of below 4.0 μm, and with a Dv(90) of 6.44 μm. As can be seen, the distribution by volume is dramatically affected by the fan speed reduction, resulting in a far lower range of diameters.

It is of particular interest in the present case to produce a fog in which a substantial portion of the particles are less than a desired size, such as a dry fog, and the graph shows that with a fan set at full fan speed 90% of the particles have a size of 5.41 micrometers after around 3 minutes.

Presence of a delivery duct also influences the size of droplets delivered during the nebulization process, a longer delivery duct having a similar effect to having no fan. This is likely due to the longer delivery duct making it harder for heavier particles to escape the duct, as in the absence of a fan such heavier particles will have less energy and be less likely to travel far, so that fewer droplets exit the duct, and generally only the smaller droplets.

Forces between droplets of the size relied upon herein, for example hydrostatic forces or perhaps electrostatic, act to urge the droplets apart, creating a vapor pressure which increases for at least a part of a cycle of treatment, helping to maintain the cloud of fog as a suspension in the air and urging droplets, vapor and gas into the most remote and difficult to access crevices of a room or space to be treated.

The present method and system generates a cloud of cold, dry fog containing droplets of a diameter, density and vapor pressure which ensures that all target areas are bathed in a suspension of droplets that exhibit fluid like behavior, such that the droplets move randomly to fill a space or room being treated and can enter areas inaccessible to larger droplets. The range of droplet sizes and the inevitable generation of some substances in the vapor and gas states, as well as fog, ensures an efficient and comprehensively thorough delivery of the desired substance. In addition, reliance on droplets of a predetermined size such as for example but not limited to a size less than 6.31 µm diameter ensures that a smaller amount of liquid can deliver the desired comprehensive coverage of a room or space compared with prior art devices.

The presence of a fan can assist with delivery of the droplets produced to desired areas, and such a fan, or an additional fan, may be placed outside the device. A further advantage of the present method is the use of several transducers to act upon the liquid to be delivered as a cloud of fog, in particular dry fog. In particular the number of transducers used determines the time period in which a quantity of liquid may be converted into droplets of a desired size, and in which a desired vapor pressure is created within the room or space to be treated. Increasing the number of transducers converts such a quantity in a time which is significantly shorter than that achieved in prior art systems. The number of transducers can be increased to achieve a desired density of droplets of a predetermined size within a predetermined time. As an example, experiments show that each transducer can nebulize approximately 750 ml of liquid in 60 minutes, so a fog generator containing 8 transducers will nebulize 500 ml in 5 minutes, and so on.

The present method and system is directed to providing a cloud of fog, in particular a dry fog, of a desired density, and a desired droplet size within a desired time. The factors affecting this include varying an output control to determine the volume of fog to be delivered, varying a fan speed, varying a length of a delivery duct, and varying the number of transducers acting on the preparation to be nebulized into the fog. For example, a room or space with dimensions 3×6×2.5 meters (45 cubic meters) may be filled with a visibly dense cloud of dry fog, providing for a visibility of up to two meters, of up to one and a half meters, of up to one meter, or of up to a half a meter or less within several minutes of initiating nebulization of 500 ml of liquid. This may include within 25 minutes, within 15-25 minutes, within 10-15 minutes, within 5-10 minutes or within less time still of initiating nebulization using a variable number of transducers. It is contemplated that a common application would use 4, 6, or 8 or more nebulizing transducers, for example for up to 24 transducers or with two devices each with a selected number of transducers. This provides great advantages over known systems, which take a significantly longer time.

In addition in one typical experiment a 125 cubic meter room at ambient temperature took 10 minutes to fill to a desired density with a fog of a desired droplet size.

Rooms or spaces with larger dimensions can be filled in a desirably short time by adjusting the amount of liquid, the number of nebulizers, fan speed, delivery duct length and so on. A system including 24 transducers, or several devices each including a plurality of transducers, can extend the number of transducers and therefore the speed with which a space is filled. The time taken to fill a room or space to a desired density may be achieved by adjusting the number of transducers, as well as adjusting various parameters of the apparatus, such as fan speed.

An advantage of the present arrangement is that the dry fog forms and fills a room or space so quickly that the active ingredient can be delivered before the droplets evaporate. A problem with prior art systems is that the fog forms sufficiently slowly that delivery of the active agent is compromised, or is at least less efficient, as a significant portion of droplets evaporate before delivery can take place, or droplets are so large that they coalesce resulting in wetting. An advantage of the present system is that very large spaces can also be filled with a dry fog and treated, for example sports stadiums and such like.

Table 2 shows sample measurements relating to room or space size, amount of solution used, number of transducers used and time taken to produce a visibly dense cloud of fog.

TABLE 2

| Room or space size (m³) | Volume of soln (ltr) | No transducers used | Density of fog (visibility in m) | Time to fill (minutes) |
| --- | --- | --- | --- | --- |
| 45 | 0.5 | 8 | 1 | 5.5 |
| 75 | 2 | 8 | 1 | 15 |

As stated, the present system may be used to apply preparations to crops for example salads, vegetables or potatoes in storage or in retail stores; in a clinical environment such as a hospital; in a laboratory or containment room; or in other environments in which biological material such as micro-organisms, pathogenic material, contaminants, spoilage or other material, needs to be contained or neutralized.

Such environments could include any areas where people or animals gather for entertainment, to consume food or beverages, travel or to wait, such as for example cinemas, theatres, sports halls and stadiums, parks including amusement parks and playgrounds, schools, lecture halls, laboratories, museums, hotels, restaurants, food halls, supermarkets and other retail outlets, waiting rooms, booking halls, trains, aircraft, coaches, lorries, ships, ambulances, stations, airports, coach stations, office blocks, hotels, air-conditioning systems, hospitals, loading areas, warehouses, farms, abattoirs, any food preparation or storage areas, medical or veterinary environments, and such like. The device may be helpful in maintaining areas for burns victims, including areas where burns victims may be placed for exposure to a cool and disinfecting, and non-invasive fog.

The present system may also be used in plant propagators, for example in combination with aeroponic or hydroponic systems. The preparation provided in the fog may then be a nutrient rich solution to be provided as a fog of a desired droplet size and density to bathe the roots and/or leaves in such plant propagators. The fog may be provided for an extended period of time to reflect the need to attend to such plants during their lifetime, including feeding them. In use, in the present device a suitable number of transducers are arranged within a shallow reservoir containing a solution, for example a decontaminating solution. The solution may include, for example, hydrogen peroxide solution, a chlorine solution, chlorine dioxide solution, formaldehyde, electrochemically activated solution (ECAS) or electrolyzed water, and/or other suitable solutions. Use of the present method is suitable for treating, for example cleaning, sterilizing, sanitizing, disinfecting, decontaminating, neutralizing, hydrating, sprout suppressing, and/or feeding, an enclosed space such as a room, hall, a cabinet within a room, or a space such as a stadium, station or such like.

An electro chemically activated solution (ECAS) comprises an inert saline solution which is activated by electrochemical means. The activated solution is placed in the reservoir of the fogger and nebulized to produce a dry fog. When the ECAS meets with organic matter it produces the desired anti-microbial effect and reverts to a saline solution. Such a saline solution and other know decontaminants are damaging for some materials such as metals, and may be sufficiently acidic to be potentially harmful for a range of equipment. It is contemplated that the device of the present arrangement is formed from suitable material to avoid any such problems.

If the solution to be delivered is simple, for example delivery of a sprout-suppressing preparation to vegetables such as potatoes, or if levels of toxicity are acceptable or within safe exposure limits for humans or animals, the present method is suitable for an enclosed, but not a sealed, space. If the solution to be delivered is more toxic, such as hydrogen peroxide, chlorine, chlorine dioxide or such like, the present method is suitable for spaces which may be sealed to protect the environment and any persons in the area. Examples include a room in a hospital suitable for accommodating a patient, needing to be cleaned to eliminate an infection such as, for example, Methicillin Resistant *Staphylococcus aureus* (MRSA), or a treatment room, operating theatre or some such. The present method is also suitable for use where a still further level of isolation is needed, such as, for example, in a laboratory containment room or similar. It is contemplated that the present arrangement is also effective against Vancomycin Resistant *Enterococcus faecalis* (VRE), or other contaminants such as *Bacillus subtilis* (anthrax surrogate), *Bacillus cereus* (anthrax surrogate), *Pseudomonas aeruginosa*, or others.

This is an effective method of destroying micro-organisms, for example pathogenic micro-organisms, present in the air. Such micro-organisms present on surfaces are also rendered biologically inactive on contact with a droplet of the nebulized fog, however, the larger droplets of prior art systems tend to settle on surfaces during condensation or following contact and this can result in the formation of a film of liquid on the surface. Such a liquid film can create a barrier between the active ingredient and any contaminant remaining, for example a micro-organism, on the surface, in particular if the active agent has been delivered rendering barrier liquid ineffective. Such larger droplets cannot access smaller crevices, and may even block access to smaller crevices. A reservoir of micro-organisms or infection may therefore be created or remain which prior art systems cannot eradicate. In addition larger droplets tend to fall to the floor, or can be absorbed or remain on surfaces, causing them to become damp, wet and potentially damaged.

Droplets of the predetermined diameter, for example but not limited to droplets of a size less than 6.31 μm diameter, retain their integrity more strongly than larger droplets and so, while droplets in the cloud of dry fog touch all surfaces there is minimal coagulation and wetting. Any micro-organism on a touched surface will be rendered inactive by action of the decontaminant in a droplet, however such droplets will form only a layer of micro-condensation which is negligible and transient, and does not form a barrier to the action of further droplets. As a consequence further droplets may interact with micro-organisms on the surface, rendering them biologically inactive. In addition treated areas are lightly and transiently damped rather than wetted by exposure to the cloud of dry fog. Any light dampness dries out over a negligible time period leaving a treated room or space and its contents usable within a shorter period of time compared to known methods.

The smaller droplets of the present system are so light that, once they exit the delivery duct of the device, they remain suspended in the air for several minutes without significant velocity unless directed by an external fan as required. One measure of droplet density is the reduction in visibility, and in the present system a target visibility indicating sufficient density is between 0.5 and 2 meters, for example around one meter, or more particularly around 0.5 meters, although a more dense fog with a visibility of less than 0.5 metres may be preferable. The present method and system also produces an appropriately uniform droplet density due to a broadly homogenous droplet distribution and this is apparent due to the lack of visible stratification of the droplet cloud. Stratification of fogged clouds is common in prior art systems; however the present system has particles which, due to their small size, are not inclined to coagulate and form larger heavier droplets which cause stratification and fall to the floor to cause wetting.

Advantageously, the present method and system does not need to rely on heat vaporized or gas disinfectant to achieve the desired effect. In addition, the present method and system does not rely on fans in a room or space to blow the cloud of fog around or on personnel to direct fog around the room or space, in contrast with prior art systems, although such can be useful in certain cases. It simply fills the room or space with a visible, suitably uniformly dense, ambient temperature dry fog of a suitable velocity, which is effectively still and suspended in the air for the desired treatment time and which, due not least to vapor pressure, accesses all areas including the most inaccessible crevices.

A fan system may optionally be utilized to gently agitate the cloud of fog to encourage movement of the droplets around the room or space, additionally replacing neutralized droplets with new unused droplets to encourage complete decontamination and also to further encourage the droplets into the least accessible places, and help droplets to reach all parts of irregular shaped rooms or places.

Optionally, if further and deeper de-contamination is required, especially in areas of concern or areas which are considered harder to access, a hand held device comprising for example a flexible hose or suchlike may be provided to direct additional fog gently into particular areas before or after the first main fogging process has been completed if, for example, there is concern that the virulence of the micro-organism merits this, for particularly hard to reach areas, or for more targeted decontamination of areas or personnel. A delivery duct can be provided which is a flexible hose rather than a rigid chimney to facilitate this.

At normal ambient room temperature the cold, dry cloud of fog may remain for a period of time after the nebulizers are switched off, which advantageously provides the active agents with the opportunity to be fully effective, and this period can be at least 5 minutes, and may be 10 minutes, 20 minutes, 30 minutes or more. It is expected that the room or space will have been completely decontaminated by the end of this period.

Figure 3:
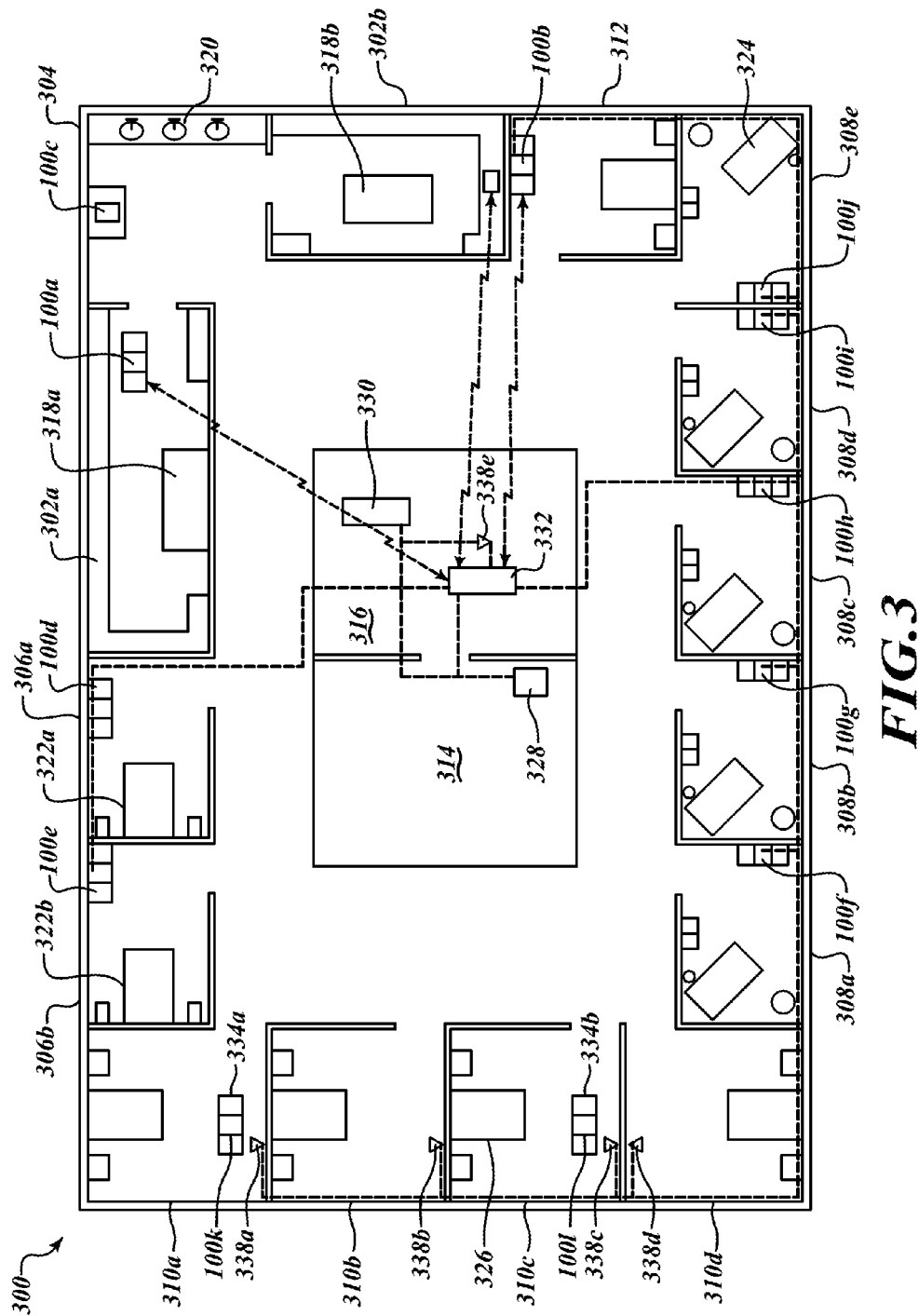
FIG. 3 is a top plan view of a medical facility including a plurality of rooms or volumes in which disinfection systems are or may be installed according to one illustrated embodiment, and further illustrating a communications network communicatively associated with the disinfection systems and with other systems of the medical facility.

FIG. 3 shows a medical facility 300 in which the disinfection system 100 (FIGS. 1 and 2) may be employed, according to one illustrated embodiment.

The medical facility 300 may take any of a variety of forms, for example, hospitals, clinics, doctor or physician offices, delivery or birthing centers, emergency or urgent care facilities, to name just a few. The medical facility 300 may include one or more rooms, volumes or spaces in which disinfection systems are installed or may be removably located to perform sterilization, disinfection or sanitization. For example, the medical facility 300 may include surgical rooms or theaters 302a, 302b (collectively 302), prep or scrub rooms 304, delivery rooms 306a, 306b (collectively 306), examination rooms 308a-308e (collectively 308), patient rooms 310a-310d (collectively 310), diagnostic imaging room 312. The medical facility 300 may include additional rooms or spaces, such as a nurse's station 314, a file and/or server room 316, waiting rooms, laboratory (not shown), locker room (not shown), supply rooms (not shown), medical imaging rooms (not shown), and other rooms or spaces commonly found in such facilities.

The rooms may include certain furnishings, fixtures, and/or equipment, as is commonly found in such rooms. For instance, a surgical room or theater 302 may include a table 318a, 318b for a patient, counters or tables, and various pieces of equipment related to monitoring patient vital signs, administering anesthetic, performing surgeries and imaging. A surgical prep or scrub room may include sanitizers, sinks 320, supplies, tables, counters, and/or chairs. A delivery room 306 may include a bed for a patient 322a, 322b, counters or tables, and various pieces of equipment related to monitoring patient vital signs, administering anesthetic, performing deliveries and imaging. Examination rooms 308 may include a table for a patient 324 (only one called out), counters or tables, and various pieces of equipment related to monitor patient vital signs, performing diagnostic and/or therapeutic examinations and imaging. A patient room 310 may include a bed for a patient 326 (only one called out), counters or tables, and various pieces of equipment related to monitoring patient vital signs, administering various therapeutic and/or diagnostic treatments. The nurse's station 314 may include a counter, desks, computers 328 (only one illustrated), and files. The server or file room 316 may, for example, include a scheduling computer system 330 used to schedule use of the various rooms. The server or file room 316 may, for example, include a disinfection system server computer system 332 which may be communicatively coupled to one or more disinfection systems 100 and configured to provide for compliance monitoring and reporting, exception monitoring and reporting, as well as other functions, described in detail below.

As illustrated in FIG. 3, at least some of these rooms may have a respective disinfection system 100a-100l (collectively 100). In some situations, the disinfection system 100 is located in the room on a permanent basis, for example on a piece of furniture or other fixture. That is, the disinfection system is not intended to be moved from room to room. In other situations, the disinfection system 100k, 100l may be located on a wheeled cart or chassis 334a, 334b (collectively 334) or other carriage, with the intent that the disinfection system 100k, 100l will be moved from room to room as needed. For example, the wheeled cart 334 may carry the disinfection system 100, one or more tanks of biocide agent and/or a fluid (e.g., water), equipment such as a spray, wand, hose or tubing, wipes or cloths, brushes, spray bottles and other sanitizers or disinfectants. The rooms may also include a separate heater or other warming device, which may be operated to facilitate dispersal of the dry fog.

The medical facility 300 may include a wire communications conduit 336 which may provide a wired communicatively path between at least some of the disinfection systems 100 and the disinfection system server 332. The medical facility 300 may include one or more antennas 338a-338e (collectively 338) which may provide a wireless communicatively path between at least some of the disinfection systems 100 and the disinfection system server 332. Explanation of the interaction between the disinfection systems 100 and the disinfection system server(s) 332 are discussed below with reference to the various flow diagram.

Figure 4:
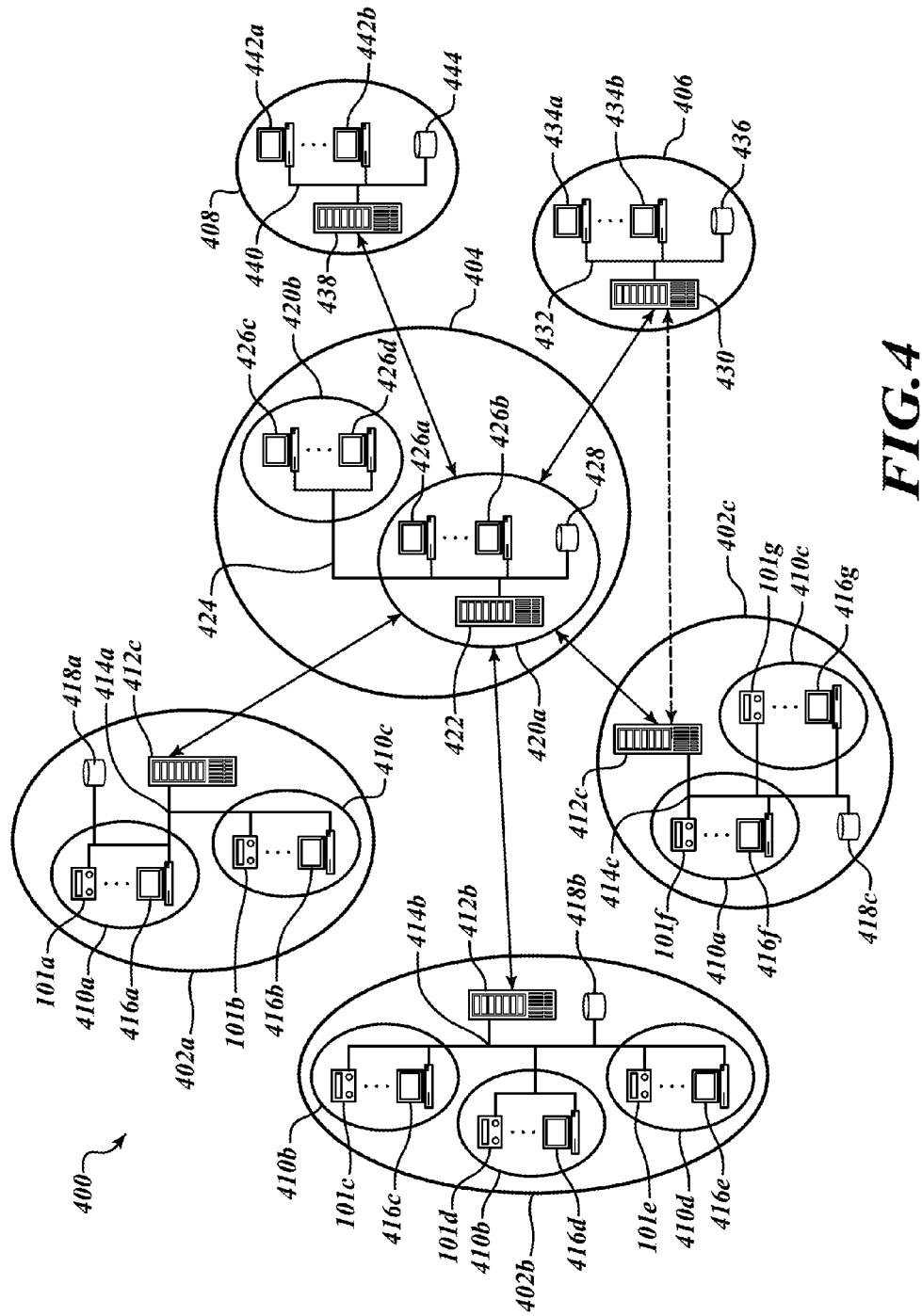
FIG. 4 is a schematic diagram of a networked environment, according to one illustrated embodiment, including a number of server computer systems associated with a number of medical facilities, a corporate management facility, an insurer facility, and a governmental organization facility.

FIG. 4 shows a networked environment 400 in which the disinfection systems and the disinfection system server(s) of FIG. 3 may be employed, according to one illustrated embodiment.

The networked environment 400 may encompass a number of medical facilities (e.g., hospitals, clinics, doctor or physician offices, delivery or birthing centers, emergency or urgent care facilities) 402a-402c (three illustrated, collectively 402), a corporate management facility 404 (one illustrated), an insurer facility 406 (one illustrated), and a governmental organization facility (e.g., Health Department, Center for Disease Control) 408 (one illustrated).

The medical facilities 402 may be organized into various units, subunits, for instance departments such as primary care 410a, surgery 410b, labor and delivery 401c, and intensive care 410d departments. As explained above the medical facilities 402 may include one or more disinfection system server computing systems 412a-412c (collectively 412). The entire medical facility 402 may share a disinfection system server computing systems 412, or some or all departments may have an associated disinfection system server computing system 412. Each medical facility may have one or more communications networks 414 (e.g., local area network or LAN) including a number of disinfection systems 100a-100g (seven illustrated in FIG. 4) and computer systems 416-416g (seven illustrated in FIG. 4). The disinfection system server computing systems 412 may include, or be communicatively associated with, one or more non-transitory storage mediums 418a-418c (collectively 418). The non-transitory storage mediums 418 may store information related to the operation of the disinfection systems 100, for instance in a database form. While not illustrated in FIG. 4, the medical facilities may include scheduling server computing systems 330 (FIG. 3), which may be communicatively coupled to the disinfection system server computing systems 412.

The various networks 414 may be communicatively coupled as, or via, a network (e.g., wide area network or WAN). As will be recognized by one of ordinary skill in the art, the medical facilities may employ other networked and non-networked communications architecture.

The corporate management facility 404 may oversee operation of one or more medical facilities 402. The corporate management facility 404 may be organized into various units, subunits, for instance departments, such as an accounting department (not shown), compliance department 420a, and executive management department 420b. The entire corporate management facility 404 may share one or more corporate management server computing systems 422, or some or all departments may have an associated corporate management server computing system 422. The corporate management facility 404 may have one or more communications networks (e.g., LAN) 424 including computer systems 426a-426d (four illustrated, collectively 426). The corporate management server computing systems 412 may include, or be communicatively associated with, one or more non-transitory storage mediums 428. The non-transitory storage media 428 may store instructions and information related to trend analysis and/or tracking, compliance analysis and/or reporting, and/or exception analysis and/or reporting.

The insurer facility 406 may likewise be organized into various units, subunits, for instance departments, for instance, accounting department (not shown), compliance (not shown), actuarial department (not shown) and executive management department (not shown). The entire insurer facility 406 may share one or more insurer server computing systems 430, or some or all departments may have an associated insurer server computing system 430. The insurer facility 406 may have one or more communications networks (e.g., LAN) 432 including computer systems 434a-434b (two illustrated, collectively 434). The insurer server computing systems 430 may include, or be communicatively associated with, one or more non-transitory storage mediums 436. The non-transitory storage media 436 may store instructions and information related to trend analysis and/or tracking, compliance analysis and/or reporting, and/or exception analysis and/or reporting.

The governmental organization facility 408 may likewise be organized into various units, subunits, for instance departments, for instance, accounting department (not shown), compliance (not shown), actuarial department (not shown) and executive management department (not shown). The entire governmental organization facility 408 may share one or more governmental organization server computing systems 438, or some or all departments may have an associated governmental organization server computing system 438. The governmental organization facility 408 may have one or more communications networks (e.g., LAN) 440 including computer systems 442a-442b (two illustrated, collectively 442). The governmental organization server computing systems 444 may include, or be communicatively associated with, one or more non-transitory storage mediums 444. The non-transitory storage media 444 may store instructions and information related to trend analysis and/or tracking, compliance analysis and/or reporting, and/or exception analysis and/or reporting.

The various server computing systems 412, 422, 430, 438 may be communicatively coupled via a WAN, such as the Internet, an extranet, intranet or other communication architecture.

FIG. 5 shows a high level method 500 of operating a disinfection system to exhaust and then extract a dry fog or biocide agent(s) into an ambient environment, according to one illustrated embodiment.

At 502, the disinfection system starts a disinfection cycle. For example, the disinfection system may start a disinfection cycle in response to an application of power or a powering up event for the disinfection system. Alternatively, the disinfection system may start a disinfection cycle in response to manual activation of a switch or user input device (e.g., user selectable icon on a graphical user interface). Additionally or alternatively, the disinfection system may start a disinfection cycle in response to an occurrence of an event, for example the occurrence of a date and/or time. The date and/or time may be associated with a scheduled procedure, for example a medical procedure, to be performed in the environment (e.g., room) in which the disinfection system is located. For instance, the disinfection system may include an internal scheduling subsystem which may store scheduling information for the environment in a physical or non-transitory computer- or processor-readable storage medium. The disinfection system may, for example, include a real time clock which tracks date and/or time in the real world, and/or may periodically receive signals indicative of date and/or time in the real world. The disinfection system may compare scheduled dates and times with real world dates and times to automatically determine when to start a disinfection cycle. Additionally or alternatively, the disinfection system may start a disinfection cycle in response to a signal received from another system, for example a signal received from an external scheduling system.

The disinfection system may perform a number of operations upon powering or starting up, or prior to each detection cycle. For example, the disinfection system may enter a Power-Up mode, and turn ON or illuminate a power indicator (e.g., LED), which may remain ON or illuminated as long as the power is applied and a power switch is in the ON state. For example, the disinfection system may perform software initialization, built in tests, and an audio/visual test. If a fault is detected, the software may progress to a system fault mode. If no faults are detected, the software may turn ON a system ready indicator (e.g., LED green), and either start a detection cycle or enter a ready mode from which a detection cycle may be triggered either by an end user input or in response to an event. In the system fault mode, the software may cause an indication of the detection of a system fault by blinking a system ready indicator (e.g., LED) yellow, and/or issuing a sequence of rapid beeps or other sounds. The corrective action for the system fault mode may be to cycle power to reinitiate the power up mode.

At 504, the disinfection system nebulizes at least one biocide agent during a first portion of the disinfection cycle. The disinfection system may employ a variety of structure and/or methods to nebulize the biocide agent(s). One such method is described below with reference to FIG. 13. A metering mechanism 206 (FIG. 2) may meter a desired or defined amount of one or more biocide agents to a transducer 208 from one or more biocide reservoirs 202. The disinfection system may cause the transducer 208 to vibrate or oscillate at one or more desired or defined frequencies to nebulizer the biocide agent. For example, the disinfection system may cause the transducer 208 to vibrate or oscillate for a set or defined amount of time to nebulize biocide agent(s). Such may be fixed at a factory or programmed at a facility but is not generally changeable by the end user.

Alternatively, the disinfection system may cause the transducer to oscillate or vibrate for an amount of time either entered by an end user or for a time determined by end user operation (e.g., end user turning the disinfection system or nebulizer ON and OFF).

Alternatively, the disinfection system may cause the transducer to oscillate or vibrate for an amount of time that varies based a feedback signal from one or more sensors. Such may, for example, be based on an effectiveness of the nebulization. For example, the disinfection system may include one or more sensors and/or receive signals from one or more sensors which may be indicative of an effectiveness of the nebulization. For instance, the sensors may sense and indicate a volume and/or size of biocide agent nebulized and/or a volume or concentration of nebulized biocide agent exhausted into the ambient environment.

As previously discussed, the disinfection system may distribute a single biocide agent, or may distribute two or more biocide agents, either concurrently or sequentially. Thus, the metering mechanism may be operated to meter a single biocide agent to the transducer at a time, in a preprogrammed order or in an order that is selected by an end user or otherwise defined. Alternatively, the metering mechanism may meter two or more different biocide agents to the transducer concurrently.

At 506, the disinfection system distributes the nebulized biocide agent(s) into the ambient environment from the disinfection system. The disinfection system may employ a variety of structure and/or methods to distribute the nebulize the biocide agent(s). One such method is described below with reference to FIG. 13. For example, the disinfection system may actively propel the nebulized biocide agent(s) into the ambient into the environment via a blower or other type of exhaust fan 212 (FIG. 2). The exhaust fan 212 may, for example, operate for a set or defined amount of time. Such may be fixed at a factory or programmed at a facility but is not generally changeable by the end user. Alternatively, the exhaust fan 212 may operate for an amount of time either entered by an end user or for a time determined by end user operation (e.g., end user turning the disinfection system or fan ON and OFF). Alternatively, the exhaust fan 212 may operate for an amount of time that varies based a feedback signal from one or more sensors. For example, the disinfection system may include one or more sensors and/or receive signals from one or more sensors which may be indicative of volume, size and/or concentration of nebulized biocide agent exhausted into the ambient environment. Thus, the exhaust fan 212 may operate, for example until a concentration of biocide agent(s) in the ambient environment or in the dry fog exhausted into the ambient environment exceeds a defined threshold At 508, the disinfection system extracts or withdraws the dry fog from the ambient environment into the disinfection system during a second portion of the disinfection cycle. The disinfection system may employ a variety of structure and/or methods to withdraw or extract the dry fog from the ambient environment. One such method is described below with reference to FIG. 13. For example, the disinfection system may actively withdraw or extract the dry fog from the ambient into the environment via a blower or other type of extraction fan 214 (FIG. 2). The extraction fan 214 may, for example, operate for a set or defined amount of time. Such may be fixed at a factory or programmed at a facility but is not generally changeable by the end user. Alternatively, the extraction fan 214 may operate for an amount of time either entered by an end user or for a time determined by end user operation (e.g., end user turning the disinfection system or extraction fan ON and OFF). Alternatively, the extraction fan 214 may operate for an amount of time that varies based a feedback signal from one or more sensors. For example, the disinfection system may include one or more sensors and/or receive signals from one or more sensors which may be indicative of volume, size and/or concentration of nebulized biocide agent remaining in the ambient environment or in dry fog withdrawn or extracted therefrom. Thus, the extraction fan 214 may operate, for example until a concentration of biocide agent(s) remaining in the ambient environment or in the dry fog withdrawn or extracted from the ambient environment falls below a defined threshold.

At 510, the disinfection system ends the disinfection cycle. For example, the disinfection cycle may end a defined time after the disinfection cycle starts. Alternatively, the disinfection cycle may end in response to activation of a switch by an end user selection or selection of a user selectable icon, or on stopping a supply of power to the disinfection system. Alternatively, the disinfection system 100 may end the disinfection cycle in response to one or more measured, sensed or determined values or parameters achieving a condition relative to a threshold level. For example, the disinfection system 100 may end the disinfection cycle in response to a concentration of dry fog or biocide agent in the ambient environment reaching a defined concentration. Alternatively, or additionally, the disinfection system 100 may end the disinfection cycle in response to a concentration of dry fog or biocide agent exhausted from the disinfection system reaching a defined concentration. Alternatively, or additionally, the disinfection system 100 may end the disinfection cycle in response to a desired level of biocide agent, wetness or relative humidity in the ambient environment being measured, sensed or otherwise determined, and/or in response to some other value, parameter or condition, for instance a suitable result from one or more pathogen and/or organic material tests.

The disinfection system may perform successive disinfection cycles. For example, the disinfection system may be manually or automatically operated to perform a disinfection cycle immediately prior to each medical procedure and/or following each medical procedure. Such may, for example, be automatically triggered according to a schedule use of a room or other location. For instance, a scheduling system may provide signals to cause the disinfection system to start a disinfection cycle or may provide scheduling information which allows the disinfection system to trigger a disinfection cycle. Such may additionally, or alternatively, be useful in stopping the exhausting of biocide agent to the ambient environment after a first defined period, stopping the extraction of biocide agent from the ambient environment after a second defined period and/or turning the disinfection system OFF or enter a low energy consumption sleep mode after a third defined period to reduce power consumption. Alternatively, or additionally, the disinfection cycles, or portions thereof such as an exhaustion portion and an extraction portion, may be started and/or stopped based on various measured, sensed or determined values, for instance those values measured, sensed or determined using the internal and/or external sensors $S_1$-$S_{14}$.

FIG. 6 shows a low level method 600 of operating a disinfection system to exhaust a dry fog or biocide agent(s) into an ambient environment, according to one illustrated embodiment. The method 600, or portions thereof, may be implemented in performing one or more of the acts of the method 500 (FIG. 5).

At 602, the disinfection system causes a transducer to nebulize at least one biocide agent. The disinfection system may, for example, apply a signal with a varying current or voltage to cause a transducer 208 (FIG. 2) (e.g., electric motor, piezoelectric transducer, MEMs transducer, mesh or membrane transducer, oscillating or rotating magnets, jet) to vibrate or to cause a vibration in a media at one or more frequencies, for instance one or more ultrasonic frequencies. Such frequency or frequencies may be selected based at least in part on the specific physical characteristics of the biocide agent(s) to, for instance, achieve a desired particle size and/or suspension in an exhaust stream.

At 604, the disinfection system imparts the vibration to the at least one biocide agent. For example, the disinfection system may impart the vibration to the at least one biocide agent by physical contact, by jet or by any other mechanism. Alternatively, or additionally, the disinfection system may sonically impart the vibration to the at least one biocide agent by pressure fluctuations or pulses of air or other fluid medium. As discussed above the disinfection system may use any of a variety of structures to nebulize the biocide agent(s). Also as discussed above, the disinfection system may employ a variety of approaches to controlling the time period during which the biocide agent undergoes nebulization.

At 606, the disinfection system exhausts the at least one nebulized biocide agent into the ambient environment as a dry fog, for example by operating one or more exhaust fans 212 (FIG. 2). For example, the disinfection system may operate a fan in a first direction (e.g., clockwise) to propel nebulized biocide agent(s) from the disinfection system. As discussed above the disinfection system may use any of a variety of structures to exhaust the nebulizer biocide agent(s) into the ambient environment. Also as discussed above, the disinfection system may employ a variety of approaches to controlling the time period during which the biocide agent is exhausted into the ambient environment.

At 608, the disinfection system withdraws or extracts the dry fog from the ambient environment, for example by operating one or more extraction fans 214 (FIG. 2). The fan(s) 214 may be different from the fan(s) 212 as used to exhaust the nebulized agent(s) into the ambient environment. Alternatively, the fan(s) may be the same fan(s) as used to exhaust the nebulized agent(s) into the ambient environment, the impeller, blades or other air moving structure simply being run in a reverse direction. For example, the disinfection system may operate a fan in a second direction (e.g., counterclockwise) to withdraw or extract the dry fog from the ambient environment. As discussed above the disinfection system may use any of a variety of structures to withdraw or extract the dry fog from the ambient environment. Also as discussed above, the disinfection system may employ a variety of approaches to controlling the time period during which the dry fog is withdrawn or extracted from the ambient environment.

Optionally at 610, the disinfection system condenses water vapor from the dry fog extracted from the ambient environment. The disinfection system may use a variety of structures to condense water vapor from the dry fog. For example, the disinfection system may employ one or more condenser coils 228a (FIG. 2), a fluid (i.e., liquid and/or gas) heat transfer medium 228b carried in the condenser coils and a compressor 228c coupled to control a pressure of the heat transfer medium. The condensed water may be retained in a fluid reservoir 220 (FIG. 2).

Optionally at 612, the disinfection system may recycle the condensed water. For example, the disinfection system may include one or more conduits 224 (FIG. 2) fluidly communicatively coupled to direct the condensed water to other portions of the disinfection system, for example to a humidifier 218a (FIG. 2) associated with exhausting the nebulized biocide agent(s). Alternatively, the fluid reservoir 220 (FIG. 2) may be manually or automatically emptied from time-to-time.

Optionally, at 614, the disinfection system may treat the extraction stream extracted or withdrawn from the ambient environment. Such techniques may, for example, disable or inactivate the biocide agent(s) from the extraction stream. Alternatively, such may allow the recaptured biocide agent(s) to be reused. Specific techniques for treating the extraction stream are discussed below, with reference to FIG. 7.

FIG. 7 shows a low level method 700 of operating a disinfection system to extract a dry fog or biocide from an ambient environment, according to one illustrated embodiment. The method 700, or portions thereof, may be implemented in performing the treating of the extraction stream withdrawn or extracted from the ambient environment 614 (FIG. 6) of the method 600.

Optionally at 702, the disinfection system filters the extraction stream to extract therefrom any biocide agent(s) which have been withdrawn or extracted from the ambient environment. For example, the disinfection system may filter the extraction stream using one or more filters, for instance activated carbon filters 230a (FIG. 2).

Optionally at 704, the disinfection system may catalyze biocide agent(s) which have been withdrawn or extracted from the ambient environment. For example, the disinfection system may expose the extraction stream to a bed of Zeolite 230b (FIG. 2) or to a reducing agent 230c.

Optionally at 706, the disinfection system may electrostatically charge particles in the extraction stream which has been withdrawn or extracted from the ambient environment. For example, the disinfection system may operate an electrostatic charge subsystem 230d (FIG. 2) to electrostatically charge the extraction stream to charge particles of biocide agent, and extract those charged particles from the extraction stream.

Optionally at 708, the disinfection system may expose the extraction stream or biocide agent(s) which have been extracted therefrom to electromagnetic radiation. For example, the disinfection system may operate a UV light source 230e (FIG. 2) to expose the extraction stream or extracted biocide agent(s) to ultraviolet light.

The disinfection system may employ any one or more of these acts 702, 704, 706, 708, in any order, or even substantially concurrently, with or without other acts. Alternatively, the disinfection system may not employ any of these acts, or may employ other acts to treat the extraction stream or extracted biocide agent(s).

FIG. 8 shows a high level method 800 of operating a system to track operation of one or more disinfection systems, according to one illustrated embodiment.

The method 800 may be performed by the disinfection systems 100 (FIGS. 1 and 2), or additionally or alternatively by one or more separate and distinct computing systems, for instance by one or more disinfection system server computer system 332, 412 (FIGS. 3 and 4). As generally described above, the disinfection systems and disinfection system server computer systems may each include one or more processors and non-transitory storage media which stores instructions and data executable by the processors. The processor and instructions may form a number of distinct modules to process data and perform various functions. For example, instructions as executed by a controller (e.g., processor) may implement a recording module 242c (FIG. 2) to record various parameters, a compliance reporting module 242d to produce reports such as compliance reports, and an exception reporting module 242e to handle exceptions (e.g., failures, out of compliance issues or variations from expected operation or thresholds).

As described in detail below, the method may track when a given disinfection system was operated, how long the disinfection system was operated, where the disinfection system was when operated, who operated the disinfection system, and the efficacy of the disinfection. Compliance with organizational, insurer and/or government requirements, protocols or registration may require multi-variable analysis. For example, compliance may require a defined biocide concentration in contact with a surface for a defined amount or period of time. Such may additionally or alternatively, required a defined wetting requirement. Measuring, sensing or otherwise determining such parameters may assist in showing or proving compliance. Measuring, sensing or otherwise determining such parameters may also allow a feedback control to be implement, for instance automatically ending a disinfection cycle when defined parameter values are achieved. Such can reduce the time that a room is out of service or cannot be used to provide the medical services. Such may also reduce the waste or resources, including biocide agents and electrical energy.

At 801, the system performs initialization and/or handshaking routines. In particular, the system may perform self-tests, may establish identify and/or form logical relationships with the surroundings and associated equipment (e.g., external sensors $S_{10}$-$S_{14}$, wheeled cart 334), facilities and/or personnel (e.g., end user, patient, medical care provider). The system may perform handshaking, for example with the external sensors, as well as with external systems, for instance a scheduling computer system 330 (FIG. 3). The system may additionally, or alternatively perform tests of external sensors $S_{10}$-$S_{14}$ and/or equipment. Such operations may facilitate compliance and/or exception reporting.

At 802, the system receives signals at a recording module from sensor(s) indicative of dry fogging biocide disinfection operating parameters. These may include signals from the various internal and external sensors $S_1$-$S_9$, $S_{10}$-$S_{14}$ described above, for instance in reference to FIG. 2. Thus, the system may receive signals from the sensors indicative of both internal parameters or operations, as well as external measurements. Such may also include signals from various other devices or sensors, for instance signals from the machine-readable symbol reader 262 (FIG. 2), RFID reader 264 (FIG. 2) and/or clock 244 (FIG. 2). Such may be temporarily or permanently recorded to a tangible, non-transitory storage medium, for instance a computer- or processor-readable memory.

At 804, the reporting module of the system produces compliance report(s) based at least in part on the dry fogging biocide disinfection operating parameters. Compliance reports may include a variety of data related to verification of the operational condition of the disinfection system and the operation of such by one or more end users, and/or the maintenance or servicing of such by appropriate personnel. For example compliance reports may include information regarding the levels of biocide agent in various biocide reservoirs, the amounts of biocide agent(s) metered, the frequency or frequencies and/or duration of nebulization by the transducer. Also for example compliance reports may include information regarding operational status of various subsystems, for instance the fans, conditioning subsystem, treatment subsystem, and/or control subsystem including and self tests performed by the disinfection system. Also for example compliance reports may include information regarding the effectiveness of biocide exhausting or distribution, for instance concentration of biocide in the exhaust stream, concentration of biocide in the extraction stream, temperature at one or more locations, relative humidity at one or more locations, presence of biocide at one or more locations, fog concentration at one or more locations, wetness at one or more locations, and/or various other measurements such as presence or quantity of pathogens or organic material at one or more locations. Some or all of this information may represent measurements or determinations made at various times, such as at the start of each disinfection cycle, during each disinfection cycle and/or immediately following each disinfection cycle. Such may also be associated with information identifying the particular disinfection system, room or space being subjected to disinfection, facility in which the room or space is located, identity of end user (e.g., operator of disinfection system), date and time of operation or measurement, scheduled procedure for the room or space, identity of patient who will occupy the room or space.

At 806, an exception reporting module of the system identifies exceptions between at least one of the dry fogging biocide disinfection operating parameters and at least one nominal dry fogging biocide disinfection operating parameter. The exception reporting module may compare signals from any of the internal sensors, $S_1$-$S_9$ to nominal operating parameters, in order to identify any out of compliance conditions. The exception reporting module may even compare signals from external sensors $S_{10}$-$S_{14}$ to nominal parameters, in order to identify any out of compliance conditions.

Suitable thresholds may be associated with various parameters to prevent false reports of out of compliance conditions or to prevent cycling back and forth between in and out of compliance conditions. For example, one type of measured or sensed value (e.g., fan speed) may have to vary by more than ten percent from a nominal value before triggering an out of compliance condition. In contrast, another type of measured or sensed value (e.g., biocide agent concentration in exhaust stream) may have to vary only by more than one percent from a nominal value before triggering an out of compliance condition. The thresholds may be set based on the importance of the particular parameter to the disinfection and based on the sensitivity or responsiveness of the particular sensors employed.

Exception reporting may also identify exceptions based on various other sensed information, for example: location (e.g., disinfection system in unexpected location), end user (e.g., disinfection system operated by unexpected or unauthorized end user), date and/or time (e.g., disinfection system being operated at unexpected time or not being operated at an expected time), and/or procedures (e.g., disinfection system not being operated in advance of particular medical procedures and/or operated in advance of other medical procedures).

At 808, the exception reporting module of the system automatically provides a notification of the occurrence of an exception. The exception reporting module may provide notification in any one or more of a variety of ways. For example, an indication of an exception may be provided at the disinfection system at which the exception is occurring. Such may include a visual indication, for example illuminating one or more LEDs and displaying an appropriate message on an LCD. Such may additionally or alternatively include providing an aural notification via a speaker or other sound emitting device. Also for example, an indication of an exception may additionally, or alternatively, be provided remote from the disinfection system at which the exception is occurring. Such may include sending an electronic message (e.g., email, SMS), sending an aural message (e.g., automated phone call, voicemail), sending a page to one or more pagers, sending a report to one or more computers or mobile communications devices. Such may include an indication of the urgency of the identified exception, as well as an indication of the identity of the particular disinfection system and/or current location thereof, for instance including directions to the location.

At 810, an archiving module of the system archives a copy of a compliance report. The archive module preferably archives the copy of the compliance report in a date and time stamped tamper indicative form. Such may be performed in conjunction with the time stamp module 252 (FIG. 2), or with some other time stamp module associated with the system. Such provides an authenticable compliance report that allows verification of the operational parameters as well as details of the actual operation of the disinfection system, which may be logically associated with a particular room or space, facility, end user, patient, or procedure. The system may archive the copy of a compliance report to one or more suitable non-transitory storage media, which may be onsite and/or offsite.

Optionally at 812, a compliance reporting module of the system provides a copy of a compliance report to a corporate management facility 404 (FIG. 4). Such allows corporate management to track compliance across various facilities, including possibly identifying trends. The compliance reporting module may provide the copy of the compliance report in electronic form, via any variety of communications mediums, for example via telecommunications and/or computer networks. Thus, the compliance reporting module may provide the copy of the compliance report in electronic form to a server or other computer of the corporate management facility.

At 814, a compliance reporting module of the system provides a copy of a compliance report to an insurer facility 406 (FIG. 4) and/or compliance verification organization such as governmental organization facility 408 (FIG. 4). Such allows insurers and/or governmental organizations to track compliance across various organizations (e.g., medical services corporations), including possibly identifying trends. The compliance reporting module may provide the copy of the compliance report in electronic form, via any variety of communications mediums, for example via telecommunications and/or computer networks. Thus, the compliance reporting module may provide the copy of the compliance report in electronic form to a server or other computer of the insurer and/or governmental organization facility.

Figure 9:
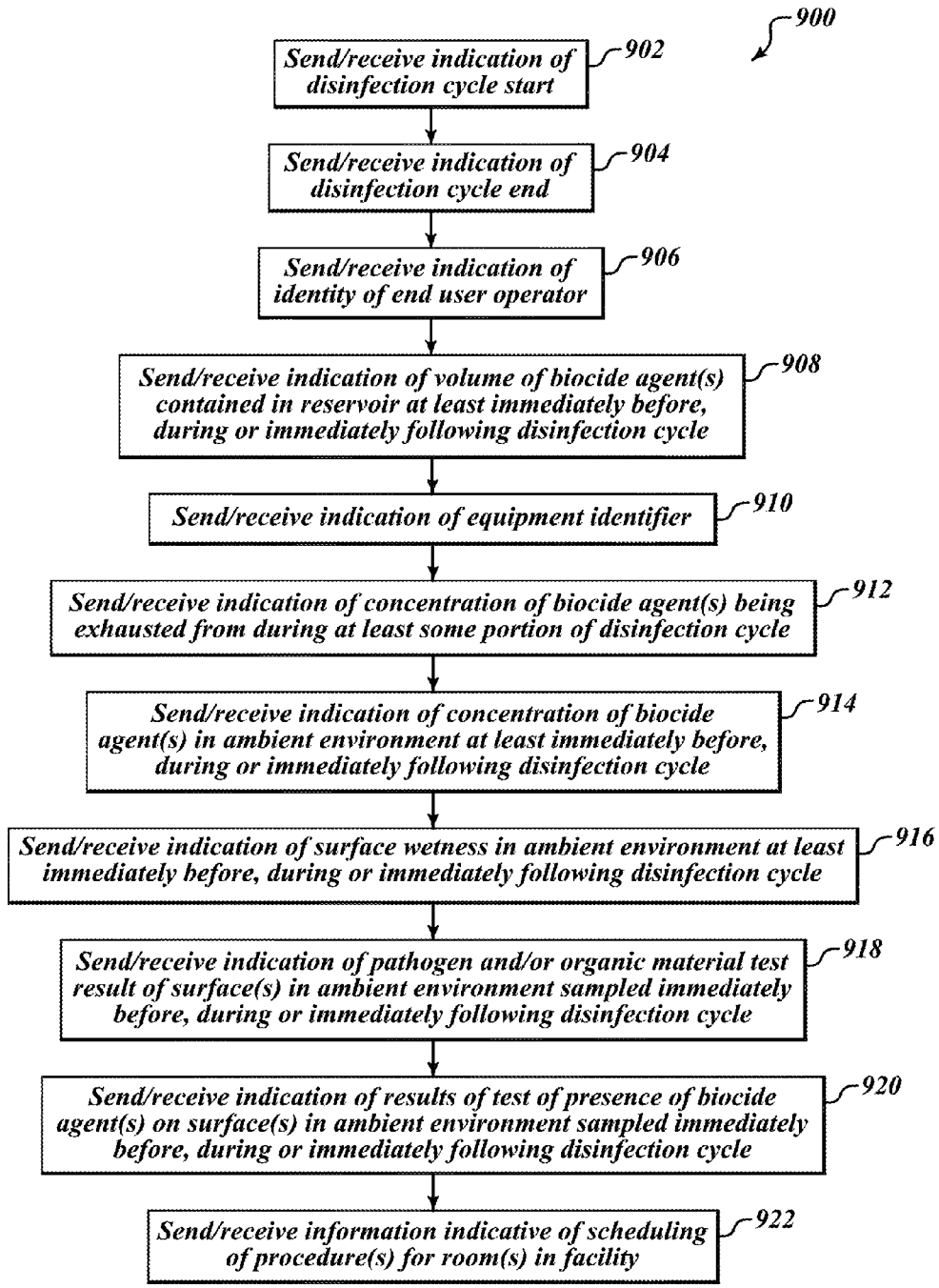
FIG. 9 is a flow diagram of a low level method of operating a system to track operation of one or more disinfection systems, according to one illustrated embodiment.
Figure 10:
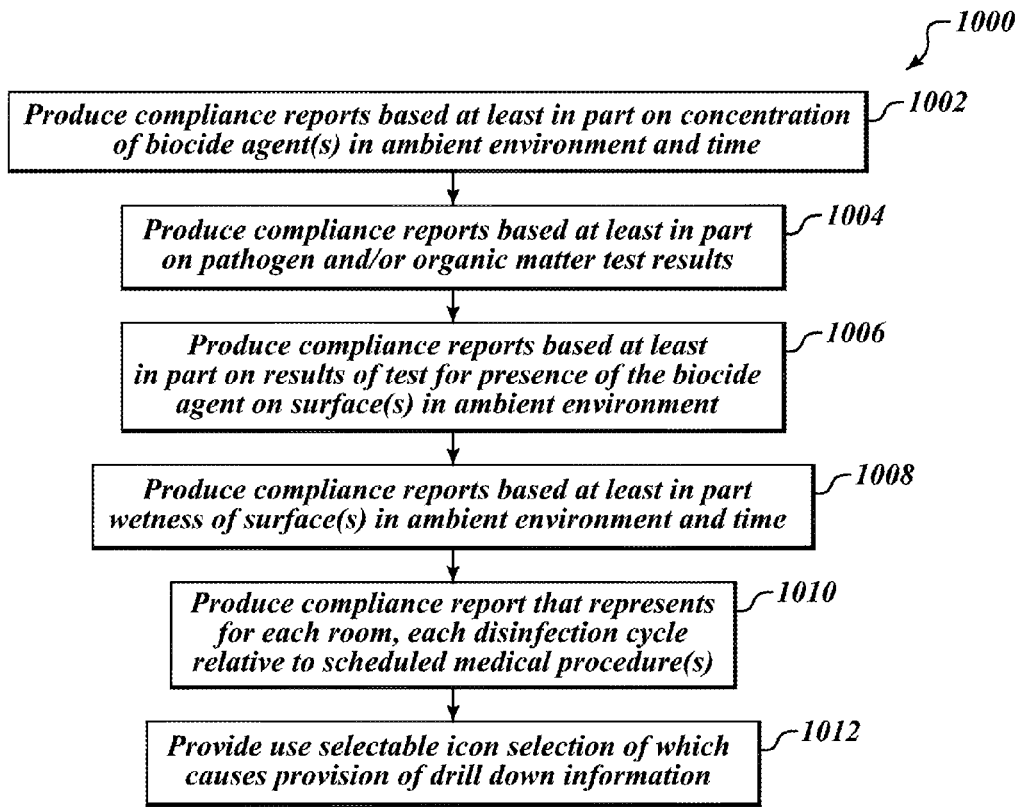
FIG. 10 is a flow diagram of a low level method of operating a system to track operation of one or more disinfection systems via compliance reporting, according to one illustrated embodiment.

FIG. 9 shows a low level method 900 of operating a system to track operation of one or more disinfection systems, according to one illustrated embodiment. The method 900, or portions thereof, may be implemented in performing one or more of the acts of the method 800 (FIG. 8).

The method 900 may be performed by the disinfection systems 100 (FIGS. 1 and 2), or additionally or alternatively by one or more separate and distinct computing systems, for instance by one or more disinfection system server computer systems 332, 412 (FIGS. 3 and 4). Thus, in the discussion immediately below a disinfection system may receive signals from various sensors. The disinfection system may store the received information, and perform exception handling. Additionally, the disinfection system may optionally transmit the information to separate and distinct computing systems, for instance by one or more disinfection system server computer systems. The separate and distinct computing systems, for instance by one or more disinfection system server computer systems may likewise receive signals from the disinfection system(s) providing the information sensed or measured by the various sensors. Thus, the specific acts of the method 900 are discussed in terms of sending or receiving, since such depends on the specific system performing the particular act.

At 902, the system sends or receives an indication of disinfection cycle start. For example, the controller 238 (FIG. 2) may receive an indication of a date and time from a clock 244, and may store such and/or may send such to an external computer (e.g., disinfection system server computer system). Establishing the start date and time can greatly facilitate verification of compliance with various sterilizing, disinfecting or sanitizing protocols.

At 904, the system receives an indication of disinfection cycle end. For example, the controller 238 (FIG. 2) may receive an indication of a date and time from a clock 244, and may store such and/or may send such to an external computer (e.g., disinfection system server computer system). Establishing the end date and time can greatly facilitate verification of compliance with various sterilizing, disinfecting or sanitizing protocols.

At 906, the receives an indication of identity of end user operator. For example, the controller 238 (FIG. 2) may receive an indication of an identifier read from a data carrier by the machine-readable symbol reader 262 (FIG. 2) and/or RFID reader 264, and may store such and/or may send such to an external computer (e.g., disinfection system server computer system). The identifier may directly identify the end user, or may provide a key to identity data stored in a table or database. Establishing the identity of the end user or operator of the disinfection system can greatly facilitate identification of the source of non compliance with various sterilizing, disinfecting or sanitizing protocols, allowing corrective or remedial actions to be taken, such as targeted training.

At 908, the system receives an indication of volume of biocide agent(s) contained in reservoir at least immediately before, during or immediately following the disinfection cycle. For example, the controller 238 (FIG. 2) may receive an indication from a biocide agent reservoir sensor $S_1$ (FIG. 2), and may store such and/or may send such to an external computer (e.g., disinfection system server computer system). Establishing levels or amounts of biocide agent in the biocide agent reservoirs can greatly facilitate verification of compliance with various sterilizing, disinfecting or sanitizing protocols. For example, such may assure that sufficient biocide agents are or were present to complete a disinfection cycle. Establishing levels or amounts of biocide agent in the biocide agent reservoirs can assist in maintenance of the disinfection systems. For example, a notification may be sent when the biocide agent reservoirs require replenishing, allowing just in time servicing.

At 910, the system receives an indication of equipment identifier. For example, the controller 238 (FIG. 2) may receive an indication of a hardwired equipment identifier, for instance from ROM 240*a* (FIG. 2), and may store such and/or may send such to an external computer (e.g., disinfection system server computer system). Establishing the identity of the disinfection system can greatly facilitate verification of compliance with various sterilizing, disinfecting or sanitizing protocols, assuring that each specific disinfection system is either in compliance or not.

At 912, the system receives an indication of concentration of biocide agent(s) being exhausted from during at least some portion of the disinfection cycle. For example, the controller 238 (FIG. 2) may receive an indication from an exhaust concentration sensor $S_9$ (FIG. 2), and may store such and/or may send such to an external computer (e.g., disinfection system server computer system). Establishing levels or concentration of biocide agent in the exhaust stream can greatly facilitate verification of compliance with various sterilizing, disinfecting or sanitizing protocols. Such may, for example, be employed with a knowledge or measurement of flow volume of the exhaust stream as well as time or duration of exhaust stream, to estimate or determine a total amount or concentration of biocide exhausted from the disinfection system during a particular disinfection cycle. Some protocols may set out an amount or concentration of biocide agent, for instance as a function of area or volume to be sterilized, disinfected or otherwise sanitized.

At 914, the system receives an indication of concentration of biocide agent(s) in dry fog in ambient environment at least immediately before, during or immediately following disinfection cycle. For example, the controller 238 (FIG. 2) may receive an indication from an ambient environment concentration sensor $S_{10}$ (FIG. 2), and may store such and/or may send such to an external computer (e.g., disinfection system server computer system). Establishing levels, densities or concentration of fog or biocide agent in the ambient environment can greatly facilitate verification of compliance with various sterilizing, disinfecting or sanitizing protocols. For example, some protocols may set out an amount or concentration of biocide agent, for instance as a function of area or volume to be sterilized, disinfected or otherwise sanitized.

At 916, the system receives an indication of pathogen and/or organic material test result (e.g., adenosine triphosphate (ATP), alkaline phosphatase (AP), pH, conductivity, temperature, protein residue test) of surface(s) in ambient environment sampled immediately before, during or immediately following disinfection cycle. For example, the controller 238 (FIG. 2) may receive an indication from an external device or computer system via one of the communications ports 256, 258 (FIG. 2), and may store such and/or may send such to an external computer (e.g., disinfection system server computer system). Establishing levels, concentration or presence of pathogens or organic material in the ambient environment can greatly facilitate assessment of the efficacy of the sterilization, disinfection or sanitization. Such may, for instance allow verification of compliance with various sterilizing, disinfecting or sanitizing protocols. For example, some protocols may set out an amount or concentration of biocide agent, for instance as a function of area or volume to be sterilized, disinfected or otherwise sanitized. Such may also allow feedback control of the disinfection system, adjusting (e.g., increasing/decreasing) any of concentration of biocide, air flow, and/or time or duration based on the levels, concentrations or presence of pathogens or organic material.

At 918, the system receives an indication of results of test of presence of biocide agent(s) on surface(s) in ambient environment sampled immediately before, during or immediately following disinfection cycle. For example, the controller 238 (FIG. 2) may receive an indication from a sensor $S_{11}$ (FIG. 2), and may store such and/or may send such to an external computer (e.g., disinfection system server computer system). Establishing presence of biocide agent on surfaces in the ambient environment can greatly facilitate assessment of the efficacy of the sterilization, disinfection or sanitization. Such may, for instance allow verification of compliance with various sterilizing, disinfecting or sanitizing protocols. For example, some protocols may set out an amount or concentration of biocide agent, for instance as a function of area or volume to be sterilized, disinfected or otherwise sanitized. Such may also allow feedback control of the disinfection system, adjusting (e.g., increasing/decreasing) any of concentration of biocide, air flow, and/or time or duration based on the levels, concentrations or presence of biocide agents in the ambient environment.

At 920, the system receives information indicative of scheduling of medical procedure(s) for room(s) in facility. For example, the controller 238 (FIG. 2) may receive an indication from an external device or computer system such as scheduling computer system 330 (FIG. 3) via one of the communications ports 256, 258 (FIG. 2), and may store such and/or may send such to an external computer (e.g., disinfection system server computer system). Establishing temporal relationships between scheduled uses of the room or space and the performance of various disinfection cycles can greatly facilitate verification of compliance with various sterilizing, disinfecting or sanitizing protocols, as well as facilitate trends analysis. Such may also allow tracking of performance of end users, determining if the end users are complying with scheduled procedures.

The system may employ any one or more of these acts 902, 904, 906, 908, 910, 912, 914, 916, 918, 920, in any order, or even substantially concurrently, with or without other acts. Alternatively, the system may less than all of these acts, not employ any of these acts, or may employ other acts to track or monitor the operational characteristics of the disinfectant system(s) and/or the effectiveness of the disinfectant system(s). For example, the system may receive and/or send information measured, collected or otherwise sensed by any of the sensors $S_1$-$S_{14}$ (FIG. 2), or automatic data collection devices 262, 264, or received via any of the communications ports 256, 258.

FIG. 10 shows a low level method 1000 of operating a system to track operation of one or more disinfection systems via compliance reporting, according to one illustrated embodiment. The method 1000, or portions thereof, may be implemented in performing one or more of the acts of the method 800 (FIG. 8).

As with the previous methods, the method 1000 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1002, a compliance reporting module of the system produces compliance reports based at least in part on concentration of biocide agent(s) in dry fog in ambient environment. The compliance reports may, for example, indicate a measured, sensed, calculated or otherwise determined concentration of biocide agent(s) in dry fog in ambient environment. The compliance reports may, for example, indicate whether the measured, sensed, calculated or otherwise determined concentration of biocide agent(s) in dry fog in ambient environment complies with some standard or meets some threshold. The compliance reports may, for example, indicate one or more of a date and time(s), identify of the particular disinfection system, location (e.g., room, space, facility), identity of the end user or operator, associated with the concentration indications.

At 1004, a compliance reporting module of the system produces compliance reports based at least in part on the pathogen and/or organic material test results. The compliance reports may, for example, indicate a measured, sensed, calculated or otherwise determined presence, level, amount, or concentration of one or more pathogens and/or organic materials in the ambient environment. The compliance reports may, for example, indicate whether the measured, sensed, calculated or otherwise determined presence, level, amount, or concentration of one or more pathogens and/or organic materials in the ambient environment complies with some standard or meets some threshold. The compliance reports may, for example, indicate one or more of a date and time(s), identify of the particular disinfection system, location (e.g., room, space, facility), identity of the end user or operator, associated with the pathogens and/or organic material test indications.

At 1006, a compliance reporting module of the system produces compliance reports based at least in part on results of test for presence of the biocide agent on surface(s) in ambient environment. The compliance reports may, for example, indicate a measured, sensed, calculated or otherwise determined presence, level, amount, or concentration of one or more biocide agents on surfaces in the ambient environment. The compliance reports may, for example, indicate whether the measured, sensed, calculated or otherwise determined presence, level, amount, or concentration of one or more biocide agents in the ambient environment complies with some standard or meets some threshold. The compliance reports may, for example, indicate one or more of a date and time(s), identify of the particular disinfection system, location (e.g., room, space, facility), identity of the end user or operator, associated with the biocide agent indications.

At 1008, a compliance reporting module of the system produces compliance report that represents for each room, each disinfection cycles relative to scheduled medical procedure(s). The compliance reports may, for example, indicate a measured, sensed, calculated or otherwise determined values or parameters for each room or space in a facility, or some subset of rooms or spaces (e.g., all surgery rooms 302 (FIG. 3), delivery rooms 306, examination rooms 308, patient rooms 310) in a facility 300. The compliance reports may, for example, indicate various scheduled and/or actual times of use of such rooms or spaces. Such may be done, for example, by patient, medical care provider, and/or use or procedure to be or actually performed in the room or space at the particular time or scheduled period. The compliance reports may, for example, indicate one or more of a date and time(s), identify of the particular disinfection system, location (e.g., room, space, facility), identity of the end user or operator, associated with the pathogens and/or organic material test indications. For instance, the compliance report may contain a schedule for each room, indicating for each period of each day in the reporting period (e.g., day, week, month, year) whether the desired or defined thresholds related to sterilization, disinfection or sanitization were met, and optionally providing additional information regarding the disinfection procedures, medical procedures and individuals associated with such. Compliance reports may include or facilitate trend analysis, that is identifying trends in compliance or lack of compliance.

Figure 11:
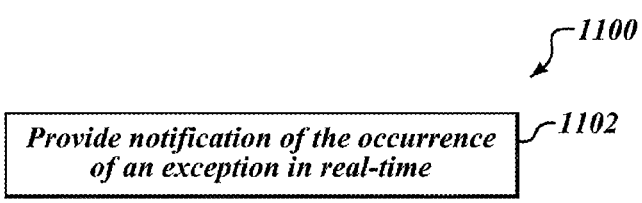
FIG. 11 is a flow diagram of a low level method of operating a system to track operation of one or more disinfection systems via real time via compliance reports employing color indicators, according to one illustrated embodiment.

FIG. 11 shows a low level method 1100 of operating a system to track operation of one or more disinfection systems via exception reporting, according to one illustrated embodiment. The method 1100 may be implemented in performing the automatically providing a notification of an occurrence of an exception 808 (FIG. 8) of the method 800.

As with the previous methods, the method 1100 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1102, an exception reporting module of the system provides notification of an occurrence of an exception in real-time.

As discussed above, the exception reporting module may provide notification in any one or more of a variety of ways. For example, an indication of an exception may be provided in real time at, proximate to, or by the disinfection system at which the exception is occurring. Such may include a visual indication, for example illuminating one or more LEDs and displaying an appropriate message on an LCD. Such may additionally or alternatively include providing an aural notification via a speaker or other sound emitting device. Also for example, an indication of an exception may additionally, or alternatively, be provided remote from the disinfection system at which the exception is occurring. Such may include sending an electronic message (e.g., email, SMS), sending an aural message (e.g., automated phone call, voice-mail), sending a page to one or more pagers, a text message to one or more mobile communications devices or computers. Such notification may include an indication of the urgency of the identified exception, as well as an indication of the identity of the particular disinfection system and/or current location thereof, for instance including directions to the location.

Figure 12:
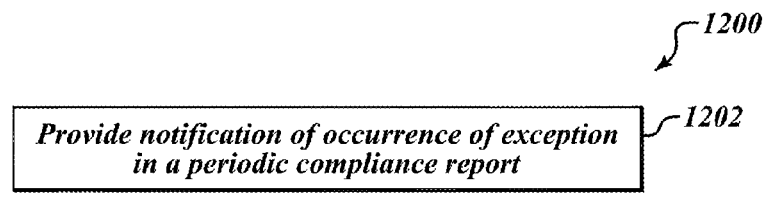
FIG. 12 is a flow diagram of a low level method of operating a system to track operation of one or more disinfection systems via periodic exception reporting, according to one illustrated embodiment.

FIG. 12 shows a low level method 1200 of operating a system to track operation of one or more disinfection systems, according to one illustrated embodiment. The method 1200 may be implemented in performing the automatically providing a notification of an occurrence of an exception 808 (FIG. 8) of the method 800.

As with the previous methods, the method 1200 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1202, an exception reporting module of the system provides notification of occurrence of exception in a periodic compliance report. For example, the exception reporting module may generate a paper, electronic or digital compliance report according to a schedule. The exception reporting module may cause electronic or digital copies to be communicated to various computer systems and/or mobile devices.

Figure 13:
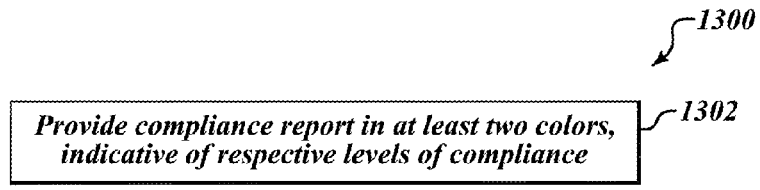
FIG. 13 is a flow diagram of a low level method of operating a system to track operation of one or more disinfection systems via compliance reports with color indicators, according to one illustrated embodiment.

FIG. 13 shows a low level method 1300 of operating a system to track operation of one or more disinfection systems via compliance reports using color indicators, according to one illustrated embodiment. The method 1300 may be implemented in performing the producing compliance reports 804 (FIG. 8) of the method 800.

As with the previous methods, the method 1300 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1302, a compliance reporting module provides a compliance report in at least two colors, indicative of respective levels of compliance. For example, values or parameters that are within defined parameters or thresholds or nominal ranges may be shown in a first color (e.g., green), while values or parameters that are outside of defined parameters or thresholds or nominal ranges may be shown in a second color (e.g., red). Additional colors may be employed. For example, a third color (e.g., yellow) for parameters or values that are in a cautionary condition.

Figure 14:
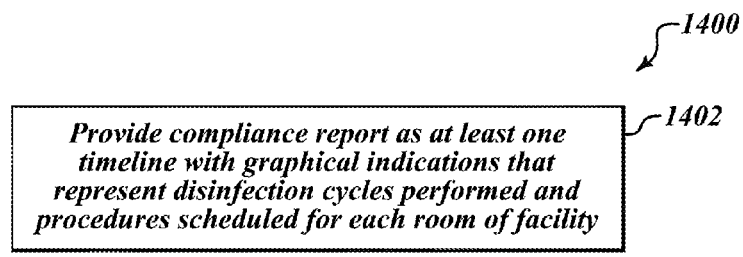
FIG. 14 is a flow diagram of a low level method of operating a system to track operation of one or more disinfection systems via timeline based compliance reports, according to one illustrated embodiment.

FIG. 14 shows a low level method 1400 of operating a system to track operation of one or more disinfection systems via timeline based compliance reports, according to one illustrated embodiment. The method 1400 may be implemented in performing the producing of compliance reports 804 (FIG. 8) of the method 800.

As with the previous methods, the method 1400 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1402, a compliance reporting module provides a compliance report as at least one timeline with graphical indications that represent disinfection cycles performed and procedures scheduled for each room of facility. Such may, for example take a form similar in format to a standard monthly calendar, for instance with months separate into days. The compliance report may allow drill down to specific days, showing for example specific time periods (e.g., hours, quarter hours) and scheduled activities for each room or space. The compliance report may allow drill down to specific time periods to provide detail reports on the various recorded parameters and values (e.g., biocide reservoir levels, nebulization parameters such as frequencies, time or amounts, biocide agent concentrations in exhaust stream, in ambient environment and/or in extraction stream, levels or presence of pathogens or organic matter) and identifiers (e.g., disinfection system identifier, end user identifiers, patient identifier, medical care provider identifier) for each time period.

Figure 15:
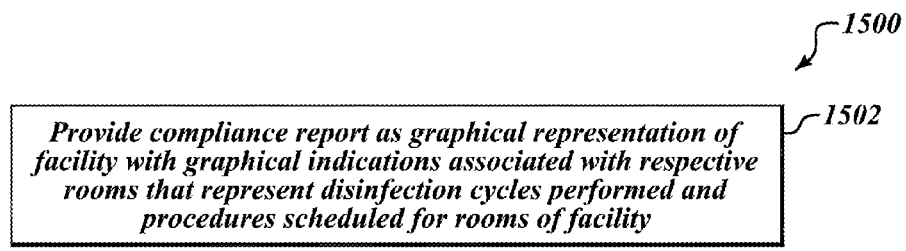
FIG. 15 is a flow diagram of a low level method of operating a system to track operation of one or more disinfection systems via graphical representation compliance reports, according to one illustrated embodiment.

FIG. 15 shows a low level method 1500 of operating a system to track operation of one or more disinfection systems via graphical representation compliance reports, according to one illustrated embodiment. The method 1500 may be implemented in performing the producing of compliance reports 804 (FIG. 8) of the method 800.

As with the previous methods, the method 1500 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1502, a compliance reporting module provides a compliance report as graphical representation of facility with graphical indications associated with respective rooms that represent disinfection cycles performed and procedures scheduled for rooms of facility. For example, the compliance report may present a schedule for a particular room or space. Procedures scheduled or which occurred in the room or space during specific time periods may be represented graphically. Various recorded parameters and values (e.g., biocide reservoir levels, nebulization parameters such as frequencies, time or amounts, biocide agent concentrations in exhaust stream, in ambient environment and/or in extraction stream, levels or presence of pathogens or organic matter) and identifiers (e.g., disinfection system identifier, end user identifiers, patient identifier, medical care provider identifier) for each time period may be displayed. Alternatively, a user selectable icon may be provided allowing a drill down screen or dialog box presenting those recorded parameters and values and/or identities.

Figure 16:
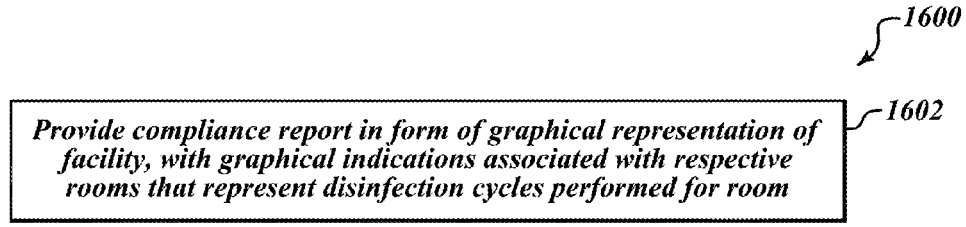
FIG. 16 is a flow diagram of a low level method of operating a system to track operation of one or more disinfection systems via graphical representation compliance reports, according to one illustrated embodiment.

FIG. 16 shows a low level method 1600 of operating a system to track operation of one or more disinfection systems via graphical representation compliance reports, according to one illustrated embodiment. The method 1600 may be implemented in performing the producing of compliance reports 804 (FIG. 8) of the method 800.

As with the previous methods, the method 1600 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1602, a compliance reporting module provides a compliance report in form of graphical representation of facility, with graphical indications associated with respective rooms that represent disinfection cycles performed for room. For example, the compliance report may represent each room, with compliance cycles (e.g., start, finish) mapped along one axis. Exceptions may be indicated in any compliance cycle in which an exception occurred.

Figure 17:
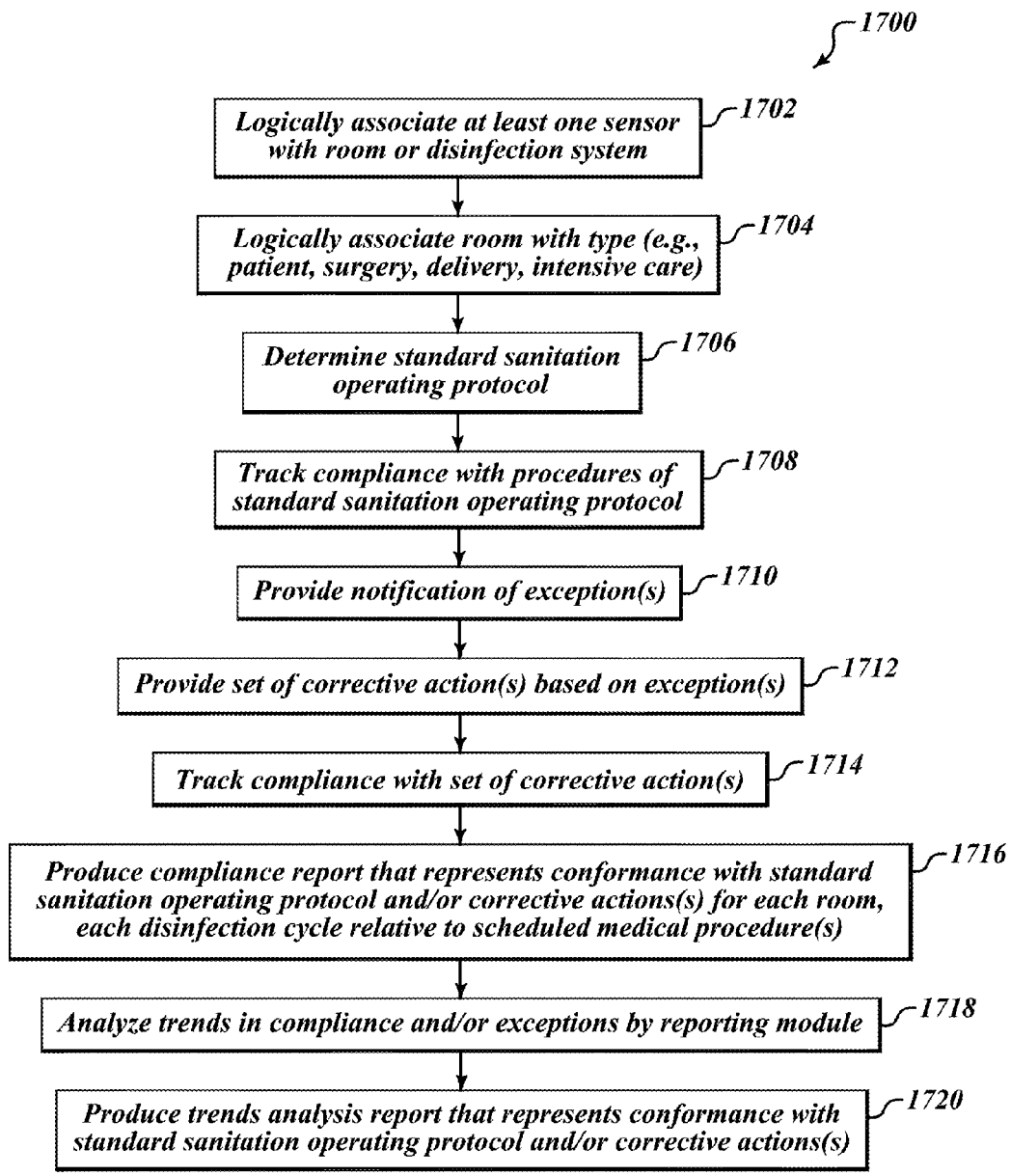
FIG. 17 is a flow diagram of an intermediate level method of operating a system to track operation of one or more disinfection systems, according to one illustrated embodiment.

FIG. 17 shows an intermediate level method 1700 of operating a system to track operation of one or more disinfection systems, according to one illustrated embodiment. The method 1700 may be implemented in performing one or more acts of the method 500 (FIG. 5).

As with the previous methods, the method 1700 may be performed by the disinfection systems 100 (FIGS. 1 and 2), or additionally or alternatively by one or more separate and distinct computing systems, for instance by one or more disinfection system server computer systems 332, 412 (FIGS. 3 and 4).

At 1702, the system logically associates at least one sensor with a room and/or a disinfection system. The system may receive signals at a recording module from sensor(s) $S_{10}$-$S_{14}$. The signals may be received, for example, as responses to interrogation signals transmitted or sent by the system. Signals may be received via wired or wireless media or via any other communications conduit or channel. For example, signals may be exchanged with the external sensors $S_{10}$-$S_{14}$ via wired or wireless communications. Signals may be exchanged with a transponder (e.g., RFID transponder or tag) attached to external sensors $S_{10}$-$S_{14}$, wheeled cart 334, room, piece(s) of equipment and/or an individual(s), for example via an RFID reader 264. Alternatively, or additionally, signals may be received from a machine-readable symbol reader 262 which signals include information that identifies external sensors $S_{10}$-$S_{14}$, wheeled cart 334, room (e.g., walls, door), piece(s) of equipment and/or individual(s).

Such may allow the system to establish a logical relationship between external sensors and a wheeled cart 334 and/or particular disinfection system 100. Such may allow the system to establish a logical relationship between a wheeled cart 334 and/or particular disinfection system 100 and a particular room.

At 1704, the system logically associates a room with a type of medical procedure. Such may allow the system to establish a logical relationship between a particular room and a type of procedure (e.g., operation, delivery, examination, patient, medical imaging) which is commonly performed in the room or a type of procedure scheduled for the room. This may, for example, include accessing scheduling information from a scheduling computer system 330 (FIG. 2) for the identified room and/or at an identified time.

At 1706, in response to identifying a specific type of procedure, the system may logically establish a particular sterilization, disinfection or sanitization protocol to be employed, for example including specific control values for controlling the disinfection system and/or parameter values to be achieved to demonstrate compliance with the sterilization, disinfection or sanitization protocol. For example, the sterilization, disinfection or sanitization protocol may dictate the concentration of biocide, time of exposure, temperature and/or relative humidity required to be achieved during a disinfection cycle. Also for example, the sterilization, disinfection or sanitization protocol may dictate the conditions to be achieved immediately following a disinfection cycle, such as temperature, relative humidity, and/or defined levels (e.g., minimum level, maximum level) of detectable biocide in the ambient environment. As a further example, the sterilization, disinfection or sanitization protocol may dictate the levels of measured, sensed or otherwise determined parameters required to demonstrate satisfactory compliance. For instance, measured, sensed or otherwise determined pathogen or organic material levels below some defined acceptable threshold, measured or sensed wetness above some defined acceptable threshold.

Establishing the logical relationship may include communicating with one or more computing systems and/or databases which store the protocol information, or may include retrieving the protocol information from a memory associated with the system.

The system may employ the logical relationships to establish additional logical relationships. For example, the system may establish logical relationships between various conditions specified by the particular sterilization, disinfection or sanitization protocol to be employed for a given room and the various internal and/or external sensors $S_1$-$S_{14}$. Also for example, the system may establish logical relationships between various conditions specified by the particular sterilization, disinfection or sanitization protocol to be employed for a given room and the external devices and/or systems, for instance reports received from a laboratory via a wired port 256, wireless port 258 or user interface 254. As discussed below in reference to FIGS. 8, 11 and 12, this allows the system to perform exception reporting, providing alarms when exceptions occur.

At 1708, the system tracks compliance with the procedures and/or values set out by the applicable sterilization, disinfection or sanitization protocol. For example, the system can determine from the internal sensors $S_1$-$S_{10}$ and clock 244 whether sufficient biocide agent(s) was available in the biocide reservoirs 202 (FIG. 2), whether suitable nebulization occurred, whether suitable flow rates were achieved, the time during which biocide agent(s) were exhausted, temperature of the exhaust stream, etc. For example, the system can determine from the external sensors $S_{10}$-$S_{14}$ and clock 244 whether sufficient concentration of biocide agent(s) was distributed into the ambient environment, temperature and/or relatively humidity of the ambient environment, surface wetness, presence or levels of pathogens and/or organic material in the ambient environment, etc. Thus, the system can determine not only whether each step in the sterilization, disinfection or sanitization protocol was performed, but whether each step was suitably performed.

At 1710, the system provides notification of exceptions if any exceptions are detected. Exceptions may take a variety of forms. For example, there may not be sufficient biocide in the biocide reservoirs 202 (FIG. 2) or there may be insufficient fluid in the fluid reservoir 220. Also for example, the speed of the fans 212, 214 may be too fast or two slow, or the flow rates may be insufficient. Also for example, sufficient nebulization may not be achieved. Also for example concentration of biocide in the exhaust stream and/or in the ambient environment may be too low or too high. Also for example, the duration of time during which biocide is exhausted may be too long or too short. The time the biocide remains in the ambient environment may be too long or short. A measured, sensed or otherwise determined parameter may be out of an acceptable range. For instance, an amount or level of pathogen or organic material detected after a disinfection cycle may be too high. A self test or test of an internal or external sensor $S_1$-$S_{14}$ may indicate a anomaly.

At 1712, upon an occurrence of an exception the system provides a set of corrective actions to be taken. For example, the system may visually and/or aurally provide one or more corrective actions to an end user via an element of the user interface 254 (FIG. 2). Such may indicate the problem as well as the corrective action. For instance, a message may indicate that one or more of the biocide reservoirs 202 need to be refilled, or that the fluid reservoir 220 needs to be refilled or emptied. Also for instance, the message may indicate that one or more components of a disinfection system needs to be cleaned or replaced. Such may include replacement of internal or external sensors $S_1$-$S_{14}$. Such may include replacement of filter(s) 230a, Zeolite 230b, reducing agent 230c, or UV light source 230e. Such may indicate a clog in conduit 224, 226, 232 or a stuck valve 222. Also for instance, a message may indicate that another complete, or even a partial, disinfection cycle should executed, either as the corrective action or following some other corrective action, such as following the refilling of the biocide reservoirs 202. Thus, for example, where the various components of the disinfection system are operating properly but a level of pathogens or organic material detected in the ambient environment following a first disinfection cycle is too high, the corrective action may consist of executing or performing a second disinfection cycle before using the room or space to perform a medical procedure. Where, for example, a component of the disinfection system was found to be out of compliance, the corrective actions may include fixing, adjusting, cleaning or replacing the component and then executing or performing a second disinfection cycle before using the room or space to perform a medical procedure.

At 1714, the system tracks compliance with the corrective actions. The system may rely on the internal and/or external sensors $S_1$-$S_{14}$, as well as external systems and components to determine whether suitable corrective actions were taken.

At 1716, the system produces a compliance report that represents conformance or lack thereof with the sterilization, disinfection or sanitization protocol and/or corrective actions. The compliance report may, for example, represent each room, each disinfection cycle relative to medical procedure scheduled for that room following each disinfection cycle. The compliance report may indicate whether each step of the sterilization, disinfection or sanitization protocol was performed and may represent various operational parameters associated with one or more of the steps, for instance biocide agents dispersed, order of dispersal, relative levels of concentration, and times associated with the various disinfection cycles, as well as the identity of the end user who operated the disinfection system. Such may also indicate whether each corrective action was preformed, parameters associated with the corrective actions, as well as the identity of the individual who performed the corrective actions. The compliance report may include or take the form of a check list of the sterilization, disinfection or sanitization protocol and/or corrective actions.

At 1718, the system automatically analyzes trends. The system may identify trends related to a particular disinfection system, a collection of disinfection systems, a particular facility, a particular medical procedure, a department or an individual. By collecting data over an extended period, application of various statistically software tools can identify short term and long term trends. Such trends may indicate a need to change or vary a particular sterilization, disinfection or sanitization protocol. Such trends may indicate a need to change or vary a set of corrective actions. Such trends may indicate a need to change or vary training procedures used to train the end users, or may identify groups or even individual end users who require remedial training.

At 1720, the system produces trends analysis report(s) that represent trends in the conformance or lack thereof with the sterilization, disinfection or sanitization protocol and/or corrective actions. The trends analysis reports may be in electronic or paper form. The trends analysis reports may be propagated through a hierarchical organization, to various levels as need. The trends analysis reports may be shared with other entities, for example insurers 406 and/or governmental organizations 408.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other environments, not necessarily the exemplary medical care environments (e.g., hospitals, clinics, physician offices, urgent care facilities, imaging or radiological facilities) generally described above. The sanitization or disinfection devices and/or tracking systems may also be useful in other environments, such as public or private facilities in which people gather, reside or are confined or in which consumable products such as food or beverages are prepared, processed, or packaged. Such environments may, for example include sports arenas or stadiums, theaters, amusement parks, museums, exhibition halls, or convention centers. Such environments may, for example, include conveyances such as trains, ships, airplanes, buses, trucks, and associated facilities such as terminals, stations, waiting areas or rooms, loading docks, or warehouses. Such environments may, for example include apartment houses or blocks, public housing, hotels, motels, barracks, or camp bunkhouses. Such environments may, for example include jails, prisons or other detention facilities. Such environments may include kitchens, factories, and various food processing or packaging facilities.

As noted above, tracking sanitization or disinfection may not only be useful in ensuring that adequate precautions are being taken, but may also be useful in defending against liability claims, as well as meeting requirements imposed by insurers and/or governmental mandates. For instance, reporting may be useful in complying with regulatory requirements mandated by the U.S. Food and Drug Agency (FDA) or in defending against product liability claims alleging inadequate food handling, preparation or packaging techniques.

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of physical signal bearing media include, but are not limited to, the following: recordable type media such as floppy disks, hard disk drives, CD ROMs, digital tape, and computer memory.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to: International (PCT) Patent Application Serial Number PCT/US2011/050715 filed Sep. 7, 2011, GB patent application Serial No. 1014820.3 filed on Sep. 7, 2010 in the name of Norman Pendred and Company Ltd., U.S. provisional patent application Ser. No. 61/433,774 filed on Jan. 18, 2011, GB patent application Serial No. 1115339.2 filed Sep. 6, 2011, and International (PCT) Patent Application Serial Number PCT/GB1011/051659 filed Sep. 6, 2011 which designates the United States, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for use in sterilization that exhausts and then extracts a dry fogging biocide agent into an ambient environment, comprising:

a recording module communicatively coupled to receive signals from at least one sensor that senses the ambient environment and at least one internal sensor that senses the extracted dry fogging biocide agent, the signals being indicative of dry fogging biocide decontamination operating parameters, including an indication of when a decontamination cycle starts, an indication of when the decontamination cycle ends, an indication of dry fogging biocide agent concentration levels during the decontamination cycle, and an indication of a dry fogging biocide agent concentration being extracted; and a reporting module that produces compliance reports based at least in part on the dry fogging biocide decontamination operating parameters indicated by the received signals.

2. The system of claim 1 wherein the signals from the at least one sensor are indicative of a concentration of a biocide agent being exhausted from a dry fogging biocide decontamination apparatus during at least some portion of the decontamination cycle.

3. The system of claim 1 wherein the recording module is further communicatively coupled to receive signals indicative of a concentration of biocide agent in the ambient environment at least one of immediately before, during or immediately following the decontamination cycle, and wherein the reporting module further produces the compliance reports based at least in part on the concentration of biocide agent in the ambient environment.

4. The system of claim 1 wherein the recording module is further communicatively coupled to receive signals indicative of at least one of a pathogen test result or an organic matter test result of at least one surface in the ambient environment sampled at least one of immediately before, during or immediately following the decontamination cycle, and wherein the reporting module further produces the compliance reports based at least in part on the pathogen or the organic matter test results.

5. The system of claim 1 wherein the recording module is further communicatively coupled to receive signals indicative of a result of at least one test of a presence of a biocide agent on at least one surface in the ambient environment sampled at least one of immediately before, during or immediately following the decontamination cycle, and wherein the reporting module further produces the compliance reports based at least in part on the result of the at least one test of the presence of the biocide agent on the at least one surface.

6. The system of claim 1, comprising:
at least one at least one processor; and
at least one non-transitory processor-readable storage medium communicatively coupled to the at least one processor and which stores at least one of processor executable instructions or data.

7. The system of claim 6 wherein the recording module is implemented by the at least one processor executing a first number of instructions stored in the at least one non-transitory processor-readable storage medium and the reporting module is implemented by the at least one processor executing a second number of instructions stored in the at least one non-transitory processor-readable storage medium.

8. The system of claim 1 wherein the system is a backend system and further comprises:
a communications interface communicatively coupled to receive information from a plurality of dry fogging biocide decontamination apparatus.

9. The system of claim 8 wherein the reporting module further archives a copy of a compliance report in a date and time stamped tamper indicative form.

10. The system of claim 8 wherein the reporting module further provides a copy of a compliance report to an insurer or compliance verification organization.

11. The system of claim 8 wherein the reporting module provide a compliance report in at least two colors, the colors indicative of respective ones of at least two different levels of compliance.

12. A dry fogging biocide decontamination system that exhausts and then extracts a dry fogging biocide agent into an ambient environment, the system comprising:
a recording module communicatively coupled to receive signals from at least one sensor that senses the ambient environment and at least one internal sensor that senses the extracted dry fogging biocide agent, the signals being indicative of dry fogging biocide decontamination operating parameters, including an indication of when a decontamination cycle starts, an indication of when the decontamination cycle ends, an indication of dry fogging biocide agent concentration levels during the decontamination cycle, and an indication of characteristics of the dry fogging biocide agent being extracted;
a reporting module that produces compliance reports based at least in part on the dry fogging biocide decontamination operating parameters indicated by the received signals;
a reservoir to hold a biocide;
at least one nebulizer coupled to receive the at least one biocide agent from the at least one reservoir and selectively operable to nebulize the received one biocide agent;
one or more fans, at least one of the one or more fans selectively operable to exhaust at least some of the nebulized biocide agent from the decontamination system into an ambient environment as a dry fog during a first portion of a decontamination cycle.

13. The system of claim 12 wherein the system includes at least one detector positioned to detect an amount of biocide agent in the reservoir.

14. The system of claim 12 wherein the system includes at least one sensor operable to detect a concentration of a biocide in the dry fog exhausted from a dry fogging biocide decontamination system.

15. The system of claim 12 wherein the system includes at least one machine-readable data carrier reader.

* * * * *